US012736532B2

(12) United States Patent
Daehnrich et al.

(10) Patent No.: US 12,736,532 B2
(45) Date of Patent: Sep. 15, 2026

(54) METHOD FOR DIAGNOSING AUTOIMMUNE GASTRITIS

(71) Applicant: EUROIMMUN Medizinische Labordiagnostika AG, Luebeck (DE)

(72) Inventors: Cornelia Daehnrich, Gross Groenau (DE); Christian Probst, Ratzeburg (DE); Lars Komorowski, Ratzeburg (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 714 days.

(21) Appl. No.: 16/686,923

(22) Filed: Nov. 18, 2019

(65) Prior Publication Data

US 2020/0191785 A1 Jun. 18, 2020

(30) Foreign Application Priority Data

Dec. 18, 2018 (EP) .................................... 18213659
Apr. 30, 2019 (EP) .................................... 19171829

(51) Int. Cl.
*G01N 33/564* (2006.01)

(52) U.S. Cl.
CPC ..... *G01N 33/564* (2013.01); *G01N 2800/062* (2013.01)

(58) Field of Classification Search
None
See application file for complete search history.

(56) References Cited

U.S. PATENT DOCUMENTS 6,790,940 B1 9/2004 Zentgraf et al.
9,250,247 B2 * 2/2016 Lee ...................... G01N 33/505
2003/0003516 A1 * 1/2003 Robinson ................ A61P 29/00 435/7.9

OTHER PUBLICATIONS

Callaghan et al. Autoimmunity. 1993. 16:289-295 (Year: 1993).*
Toh. The Autoimmune Diseases. 2020. 6th Edition. pp. 833-827 (Year: 2020).*
De Silva et al. Immunology. 1999. 96:145-151 (Year: 1999).*
Toh. Autoimmunity Reviews. 2014. 13:459-462 (Year: 2014).*
European Search Report issued on May 28, 2019 in European Application No. 18213659.8, with English translation.
Burbelo et al., 2012, PLoS ONE 7(9): e45216, 8 pages.
Chandra et al., Gastroenterology 2011; 140: 857-867.
Kontani et al., Clin. Exp. Immunol, (1992) 89, 63-67.
Lahner et al., Clinical and Translational Gastroenterology (2017) 8, e215, 9 pages.
Ma et al., Scandinavian Journal of Gastroenterology, Aug. 31, 1994, 29(9):790-794.
Scharf et al., Neurology 84, Apr. 21, 2015, 84, 8 pages.
Abe et al., "Cryo-EM structure of gastric $H^+$, $K^+$-ATPase with a single occupied cation-binding site", PNAS, vol. 109, No. 45, Nov. 6, 2012, pp. 18401-18406.
Abe Kazuhiro, "Crystal structures of the gastric proton pump reveal the mechanism for proton extrusion", Life Science, Spring 8 Research Frontiers 2018, 2018, pp. 16-17.
Toh et al., "The 60- to 90-kDa parietal cell autoantigen associated with autoimmune gastritis is a 8 subunit of the gastric $H^+$ /$K^+$-ATPase (proton pump)", Proc. Natl. Acad. Sci. USA, vol. 87, Biochemistry, Aug. 1990, pp. 6418-6422.
Exhibit 1, "His-Tag protein production and purification, A Hi-tag enables easy purification of your protein of interest", online search, Abcam plc, 1998-2023, 5 pages.
Exhibit 2, "Detectable" definition, online search, Cambridge University Press Assessment Oct. 23, 2023, 6 pages.
Abe et al., "Cryo-EM structure of gastric $H^+$, $K^+$-ATPase with a single occupied cation- binding site", PNAS, vol. 109, No. 45, Nov. 6, 2012, pp. 18401-18406 with Supporting Information 10.1073/pnas. 1212294109, www.pnas.org/cgi/content/short/1212294109_and_SI_Appendix.
Ian R. van Driel, et al., "Autoimmune Gastritis and Pernicious Anemia", The Autoimmune Diseases, Chapter 44, Elsevier Science & Technology, 2014, 20 pages.
Irun R. Cohen, et al. "Autoimmune Disease Models" A Guidebook, 1994, 6 pages.
P02686|MBP_HUMAN, Myelin basic protein OS=*Homo sapiens* OX=9606 GN=MBP PE=1 SV=3, 2002, UniProt, 1 page www.uniprot.org.
P25188|MBP_CAVPO, Myelin basic protein OS=Cavia porcellus OX=10141 GN=MBP PE=1 SV=1, 2002, UniProt, 1 page www.uniprot.org.
Jing-yie Ma, et al., "cDNA Cloning of the β-SUBUNIT of the Human Gastric H,K-ATPase", Biochemical and Biophysical Research Communications, vol. 180, No. 1, Oct. 15, 1991, pp. 39-45.
Y.-H. Song, et al., "Localization of a Pernicious Anaemia Autoantibody Epitope on the a'-Subunit of Human H,K-Adenosine Triphosphatase", Scandinavian Journal of Gastroenterology, 29:2, Jul. 8, 2009, 7 pages.
Song et al., "Localization of a Pernicious Anaemia Autoantibody Epitope on the α-Subunit of Human H, K-Adenosine Triphosphatase". Scandinavian Journal of Gastroenterology, vol. 29, 1994, received Mar. 10, 1993, pp. 122-127.

* cited by examiner

*Primary Examiner* — Anne M. Gussow
(74) *Attorney, Agent, or Firm* — Grüneberg Global IP, PLLC

(57) ABSTRACT

A method is useful for diagnosing AIG, which includes the step of detecting whether autoantibodies against the beta-subunit of the gastric $H^+/K^+$-ATPase are present or not in a sample comprising antibodies. The method utilizes a diagnostically useful carrier that contains a solid phase on which an agent for the specific capture of the autoantibody is immobilized. Furthermore, the diagnostically useful carrier includes a solid phase on which an agent for the specific capture of an autoantibody against the beta-subunit of the gastric $H^+/K^+$-ATPase is immobilized.

19 Claims, 2 Drawing Sheets

Specification includes a Sequence Listing.

METHOD FOR DIAGNOSING AUTOIMMUNE GASTRITIS

CROSS-REFERENCE TO RELATED APPLICATIONS

The present application claims the benefit to the European applications EP 18213659.8, filed on Dec. 18, 2018, and EP 19171829.5, filed on Apr. 30, 2019, both of which are incorporated by reference in their entirety.

REFERENCE TO A SEQUENCE LISTING

The present application is accompanied by an ASCII text file as a computer readable form containing the sequence listing entitled, "000890US_SL.txt" created on Oct. 14, 2022, with the file size of 43,765 bytes, which is incorporated by reference in its entirety.

BACKGROUND OF THE INVENTION

Field of the Invention

The present invention relates to a method for diagnosing AIG, comprising the step of detecting whether autoantibodies against the beta-subunit of the gastric $H^+/K^+$-ATPase are present or not in a sample comprising antibodies, with use of a diagnostically useful carrier comprising a solid phase on which an agent for the specific capture of the autoantibody is immobilized, and to a diagnostically useful carrier comprising a solid phase on which an agent for the specific capture of an autoantibody against the beta-subunit of the gastric $H^+/K^+$-ATPase is immobilized.

Discussion of the Background

It has been acknowledged that circulating autoantibodies against this $H^+/K^+$-ATPase from the parietal cells, also referred to as anti-parietal cell antibodies or APCAs for short, are diagnostic markers for autoimmune gastritis (AIG) and pernicious anaemia. AIG is a chronic disease with a prevalence of approx. 2% in the total population. In patients who suffer from other autoimmune diseases such as type I diabetes, the prevalence is up to 10%.

The $H^+/K^+$-ATPase in the parietal cells of the lamina propria mucosae of the gastric mucosa has the function of pumping protons and of thus maintaining an acidic environment in the stomach. It is a heterodimer composed of an alpha-subunit (encoded by the ATP4A gene), which contains the catalytic site and brings about ion transport, and a beta-subunit (encoded by ATP4B), which stabilizes the alpha-subunit and is required for the enzymatic activity.

Damage to the gastric mucosa, referred to as atrophic body gastritis (ABG), occurs in AIG. The degradation of the mucosa leads, then, to a reduced or absent secretion of gastric acid. Said reduced or absent secretion can also be caused by infections due to *Helicobacter pylori.*

In addition to other possible causes, an autoimmune gastritis can cause a pernicious anaemia (PA), an anaemia involving vitamin B12 deficiency. It is caused by a deficiency of intrinsic factor, a protein which binds and stabilizes the vitamin and is formed by the parietal cells, against which APCAs are directed.

For the correct treatment of an AIG or PA, it is essential to differentiate between a gastritis caused by autoimmunity and a gastritis caused by bacteria or medicaments. Incorrect treatment or lack of treatment can lead to a stomach ulcer or a stomach perforation; moreover, the risk of a stomach cancer increases.

There is therefore a need for diagnostic assays which are suitable for high-throughput use and which can detect diagnostically useful antibodies in readily available sample material from patients with highest possible diagnostic reliability, especially with highest possible sensitivity and/or specificity, particularly in comparison with assays based on the detection of an autoantibody against the alpha-subunit or the heterodimer, comprising alpha-subunit and beta-subunit, of the gastric $H^+/K^+$-ATPase.

It should be pointed out that the assay result on its own does not make a diagnosis possible, not least because samples from patients suffering from numerous other diseases such as pancreatitis or diabetes mellitus may have the autoantibody. The assay result can be interpreted by the attending physician together with other symptoms such as vitamin B12 deficiency, hyperchromic anaemia and lymphocyte-infiltration of the gastric mucosa and thus supports the diagnosis without itself providing a sufficient decision-making basis for a definite diagnosis.

What are disclosed in relation to this in the related art are ELISA and immunofluorescence assays which can detect autoantibodies against the heterodimer comprising the ATP4A-subunit and the ATP4B-subunit.

Since 2011, EUROIMMUN Medizinische Labordiagnostika AG has sold an ELISA based on purified native mammalian ATP4 comprising both subunits. In the description of the assay, the specificity is addressed in detail and it is pointed out that said specificity can be optimized via the choice of cut-off value (catalogue No. EA 1361-9601 G).

WO2011/150086 discloses the detection of autoantibodies against the ATP4A-subunit.

Wenzlau et al. disclose the detection of autoantibodies against ATP4A for the diagnosis of autoimmune gastritis in patients who suffer from type I diabetes. A radiobinding assay was used (Wenzlau, J. M., Gardner, T. J., Frisch, L. M., Davidson, H. W. and Hutton, J. C. (2011) Development of a novel autoantibody assay for autoimmune gastritis in TI D individuals, Diabetes Metab Res Rev., 27(8): 887-90).

Rusak et al. disclose that the ATP4A-subunit of the gastric $H^+/K^+$-ATPase is the major antigen for APCAs (Rusak, E., Chobot, A., Krzywicka, A. and Wenzlau, J. (2016) Anti-parietal cell antibodies—diagnostic significance, Advances in Medical Sciences, 61: 175-179). They report that better results can be achieved with radioimmunoassays than with ELISA or IFT.

Scharf et al. disclose, in connection with neurological autoimmune diseases, that it was possible to detect autoantibodies against the ATPase heterodimer using an immunofluorescence assay when cells which expressed either ATP4A or ATP4B were used (Scharf, M., Miske, R., Heidenreich, F., Giess, R., Landwehr. P., Blöcker, I., Begemann, N., Denno. Y., Tiede, S., Dahnrich, C., Schlumberger, W., Unger, M., Teegen, B., Stcker, W., Probst, C., Komorowski, L. (2015) Neuronal $Na^+/K^+$ ATPase is an autoantibody target in paraneoplastic neurologic syndrome, Neurology, 84: 1-7). In a serum from a patient with neurological symptoms, antibodies against ATP4B, but not against ATP4A, were detected. There is no disclosure of what type of antigens was exactly used and how the method was carried out.

Lahner et al. disclose the detection of autoantibodies against ATP4A and ATP4B using a luminescent immunoprecipitation system (LIPS) from samples from patients who suffered from an atrophic body gastritis. What becomes apparent is that autoantibodies against ATP4A and ATP4B can be detected nearly with the same, high sensitivity and specificity (Lahner, E., Brigatti, C., Marzinotto, I., Carabotti, M., Scalese, G., Davidson, H. W., Wenzlau, J. M., Bosi, E., Piemonti, L., Annibale, B. and Lampasona, V. (2017) Luminescent Immunoprecipitation System (LIPS) for Detection of Autoantibodies Against ATP4A and ATP4B Subunits of Gastric Proton Pump $H^+/K^+$-ATPase in Atrophic Body Gastritis Patients, Clinical and Translational Gastroenterology, 8(1):e215).

Burbelo et al. studied the occurrence of antibodies against ATP4B in patients who suffered from type I diabetes (Burbelo, P. D., Lebovitz, E. E., Bren, K. E., Bayat, A., Paviol, S., Wenzlau. J. M., Barriga, K. J., Rewers, M., Harlan, D. M. and Iadarola. M. J. (2012) Extrapancreatic Autoantibody Profiles in Type I Diabetes, PLOS ONE, 7(9):e45216).

Using samples from mice, Kontani et al. identified the alpha-subunit as major antigenic protein in AIG (Kontani, K., Taguchi, D., and Takahashi, T. (1992) Involvement of the $H^+/K^+$-ATPase alpha subunit as a major antigenic protein in autoimmune gastritis induced by neonatal thymectomy in mice, Clin. Exp. Immunol. 89, 63-67).

Using unpurified beta-subunit in the form of a cell extract, Ma et al. conclude that both the alpha-subunit and the beta-subunit bind to autoantibodies from patients with AIG. A direct comparison of the human alpha- and beta-subunits was not performed (Ma, J. Y., Borch, K. and Mardh, S. (1994) Human Gastric H,K-Adenosine Triphosphatase beta-Subunit is a Major Autoantigen in Atrophic Corpus Gastritis, Scand J. Gastroenterol 29, 790-794).

Both Lahner et al. and Burbelo et al. indicate that only an assay with particularly high sensitivity and specificity such as LIPS or a radiobinding assay is suitable for a reliable diagnosis, in comparison with solid phase-comprising assay systems, by means of which many diagnostically useful epitopes cannot be detected. No reasons are given as to why the ATP4A-subunit was not selected.

SUMMARY OF THE INVENTION

The object underlying the invention is achieved by the subject matter of following various embodiments.

1. Method for diagnosing AIG, comprising the step of detecting whether autoantibodies against the beta-subunit of the gastric $H^+/K^+$-ATPase are present or not in a sample comprising antibodies, with use of a diagnostically useful carrier comprising a solid phase on which an agent for the specific capture of the autoantibody is immobilized.
2. Method according to embodiment 1, wherein the carrier is selected from the group comprising a microtitre plate, a bead, a blot, preferably western blot, line blot or dot blot, an immunofluorescence assay carrier comprising fixed cells, preferably for a microscopic analysis, a lateral flow device, a cellulose-based polymer, a biochip, a microarray and a chromatography column material.
3. Method according to embodiment 2, wherein the diagnostically useful carrier is an ELISA microtitre plate.
4. Method according to any of embodiments 1 to 3, wherein the sample is selected from the group comprising serum, whole blood, plasma and CSF.
5. Method according to any of embodiments 1 to 4, further comprising detecting whether autoantibodies against intrinsic factor are present or not in a sample.
6. Method according to any of embodiments 1 to 5, wherein the autoantibody is a class IgG antibody.
7. Diagnostically useful carrier comprising a solid phase on which an agent for the specific capture of an autoantibody against the beta-subunit of the gastric $H^+/K^+$-ATPase is immobilized.
8. Carrier according to embodiment 7, selected from the group comprising a microtitre plate, a bead, a blot, preferably western blot, line blot or dot blot, an immunofluorescence assay carrier comprising fixed cells, preferably for a microscopic analysis, a lateral flow device, a cellulose-based polymer, a biochip, a microarray and a chromatography column material.
9. Carrier according to embodiment 8, wherein the carrier is an ELISA microtitre plate.
10. Monoclonal antibody or isolated autoantibody which binds specifically against the beta-subunit of the gastric $H^+/K^+$-ATPase, particularly preferably in purified form.
11. Method for the calibration or for the quality-control of a medical device, comprising the step of contacting the carrier according to any of embodiments 7 to 9 with a liquid comprising an antibody according to embodiment 10, preferably in known concentration, followed by the step of detecting whether the antibody is present or not in the liquid, particularly preferably with at least semi-quantitative determination of the antibody in the liquid.
12. Kit comprising the diagnostically useful carrier according to any of embodiments 7 to 9, the kit comprising one reagent or more than one reagent, preferably all the reagents, from the group comprising a wash solution, a calibrator solution, an antibody against the beta-subunit of the gastric $H^+/K^+$-ATPase, and an agent for the detection of the autoantibody, preferably a secondary antibody, even more preferably a secondary antibody against IgG antibodies, or the beta-subunit of the gastric $H^+/K^+$-ATPase or a variant thereof, preferably having a detectable label.
13. Kit according to embodiment 12, wherein the secondary antibody has a detectable label, preferably from the group comprising a label which is capable of chemiluminescence, is radioactive or comprises a detectable isotope, an enzymatically active label, a label capable of fluorescence, a compound detectable by NMR spectroscopy and a spin label, preferably a label capable of chemiluminescence, most preferably a label capable of chemiluminescence that generates a chemiluminescent signal upon incubation in a suitable chemiluminescence trigger solution.
14. Use of an agent for the specific capture of an autoantibody against the beta-subunit of the gastric $H^+/K^+$-ATPase or of the carrier according to any of embodiments 7 to 9 or of the antibody according to embodiment 10 or of a polypeptide comprising the beta-subunit of the gastric $H^+/K^+$-ATPase, preferably the extracellular domain of the beta-subunit of the gastric $H^+/K^+$-ATPase or a variant thereof or a nucleic acid coding therefor, for the highly specific diagnosis of AIG.
15. Use of an agent for the specific capture of an autoantibody against the beta-subunit of the gastric $H^+/K^+$-ATPase or of a carrier comprising the agent or of the beta-subunit of the gastric $H^+/K^+$-ATPase, preferably the extracellular domain of the beta-subunit of the gastric $H^+/K^+$-ATPase or a variant thereof or a nucleic acid coding therefor, for the production of a kit for the highly specific diagnosis of AIG.

DETAILED DESCRIPTION OF THE INVENTION

Figure 1:
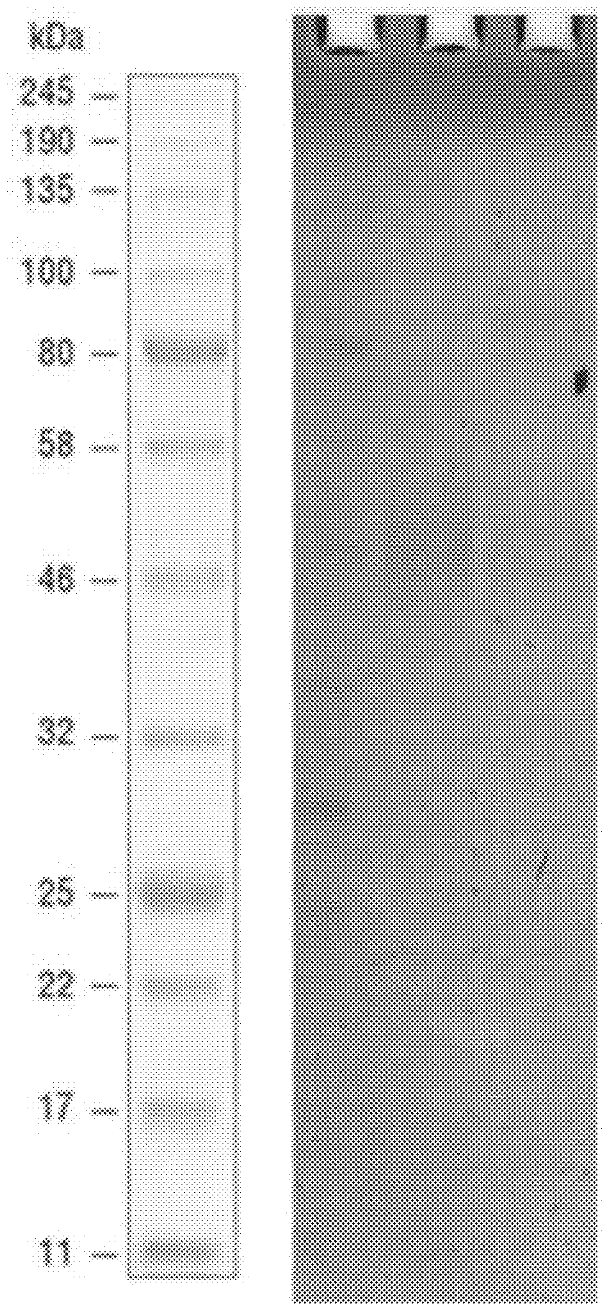
FIG. 1 shows a Coomassie-stained polyacrylamide gel, on which, to the right of the marker, 1 μg of the purified extracellular domain of the beta-subunit of the gastric $H^+/K^+$-ATPase with N-terminal His tag in a DTT-reduced state and, to the right thereof, the same in a non-reduced state have been resolved.

In a first aspect, the object underlying the invention is achieved by a method for diagnosing AIG, optionally and/or PA, comprising the step of detecting whether an autoantibody or autoantibodies against the beta-subunit of the gastric $H^+/K^+$-ATPase is or are present or not in a sample comprising antibodies, with use of a diagnostically useful carrier comprising a solid phase on which an agent for the specific capture of the autoantibody is immobilized.

In a preferred embodiment, the carrier is selected from the group comprising a microtitre plate, a bead, a blot, preferably western blot, line blot or dot blot, an immunofluorescence assay carrier comprising fixed cells, preferably for a microscopic analysis, a lateral flow device, a cellulose-based polymer, a biochip, a microarray and a chromatography column material.

In a preferred embodiment, the diagnostically useful carrier is an ELISA microtitre plate.

In a preferred embodiment, the sample is selected from the group comprising serum, whole blood, plasma and CSF.

In a preferred embodiment, the method further comprises detecting whether an autoantibody or autoantibodies against intrinsic factor is or are present or not in a sample.

In a preferred embodiment, the autoantibody is a class IgG antibody.

In a second aspect, the object underlying the invention is achieved by a diagnostically useful carrier comprising a solid phase on which an agent for the specific capture of an autoantibody against the beta-subunit of the gastric $H^+/K^+$-ATPase is immobilized.

In a third aspect, the object underlying the invention is achieved by a monoclonal antibody or isolated autoantibody which binds specifically against the beta-subunit of the gastric $H^+/K^+$-ATPase, particularly preferably in purified form, but preferably not against the alpha-subunit.

In a fourth aspect, the object underlying the invention is achieved by a method for the calibration or for the quality-control of a medical device, comprising the step of contacting the inventive carrier with a liquid comprising the inventive antibody, preferably in known concentration, followed by the step of detecting whether the antibody is present or not in the liquid, particularly preferably with at least semi-quantitative determination of the antibody in the liquid.

In a fifth aspect, the object underlying the invention is achieved by a kit comprising the inventive diagnostically useful carrier, the kit comprising one reagent or more than one reagent, preferably all the reagents, from the group comprising a wash solution, a calibrator solution, an antibody against the beta-subunit of the gastric $H^+/K^+$-ATPase, and an agent for the detection of the autoantibody, preferably a secondary antibody, even more preferably a secondary antibody against IgG antibodies.

In a preferred embodiment, the secondary antibody has a detectable label. The detectable label is preferably selected from the group comprising a label which is capable of chemiluminescence, is radioactive or comprises a detectable isotope, an enzymatically active label, a label capable of fluorescence, a compound detectable by NMR spectroscopy and a spin label, preferably a label capable of chemiluminescence, most preferably a label capable of chemiluminescence that generates a chemiluminescent signal upon incubation in a suitable chemiluminescence trigger solution.

In a sixth aspect, the object underlying the invention is achieved by use of an agent for the detection of whether an autoantibody or autoantibodies against the beta-subunit of the gastric $H^+/K^+$-ATPase is or are present or not in a sample or of the inventive carrier or of the inventive antibody for the highly specific diagnosis of AIG and/or PA.

In a seventh aspect, the object underlying the invention is achieved by the use of an agent for the detection of whether an autoantibody or autoantibodies against the beta-subunit of the gastric $H^+/K^+$-ATPase is or are present or not in a sample or of a carrier comprising the agent for the production of a kit or a composition for the highly specific diagnosis of AIG and/or PA.

In an eighth aspect, the object underlying the invention is achieved by the use of an autoantibody against the beta-subunit of the gastric $H^+/K^+$-ATPase for the diagnosis, preferably the highly specific diagnosis, of AIG. Particularly preferably, the autoantibody of the beta-subunit serves in this connection as sole biomarker, preferably as sole autoimmune biomarker in a test run, even more preferably as sole autoimmune biomarker derived from the gastric $H^+/K^+$-ATPase. This can mean that no other autoantibody is detected in parallel in the same sample, particularly no other autoantibody against the gastric $H^+/K^+$-ATPase, particularly the alpha-subunit.

The present invention is based on the surprising finding by the inventors that the detection of autoantibodies with optimized diagnostic reliability, especially specificity and sensitivity, can contribute to the diagnosis of AIG when what is detected is whether an autoantibody against the beta-subunit of the gastric $H^+/K^+$-ATPase, and not for instance against the alpha-subunit or the heterodimer, is present. This also holds true when a diagnostically useful carrier comprising a solid phase is used, i.e. assay formats which are described as diagnostically unreliable in the related art.

The present invention is further based on the surprising finding by the inventors that the detection of autoantibodies against the extracellular domain of the beta-subunit of the gastric $H^+/K^+$-ATPase allows a particularly specific diagnosis. As a result, the number of false-positive diagnoses or findings can be reduced at a high level.

In a preferred embodiment, the assay is carried out using a diagnostically useful carrier comprising a solid phase on which an agent for the specific capture of an autoantibody against the beta-subunit of the gastric $H^+/K^+$-ATPase is immobilized. In a more preferred embodiment, the agent is a polypeptide comprising the beta-subunit of the gastric $H^+/K^+$-ATPase or a variant thereof. However, molecules derived therefrom or imitating the backbone of the beta-subunit, such as peptidomimetics, peptoids, beta-peptides and peptides comprising unnatural amino acids, are also usable. A person skilled in the art is familiar with such molecules and their design (Pelay Gimeno, M., Glas, A., Koch, O., Grossmann, T. N. (2015) Structure-based design of inhibitors of protein-protein interactions: Mimicking peptide binding epitopes. *Angewandte Chemie International Edition.* 54(31): 8896-8927). It is equally possible for the beta-subunit to be detected indirectly by, firstly, detecting whether an autoantibody or autoantibodies against the heterodimer comprising alpha-subunit and beta-subunit is or are present or not and, secondly, detecting whether an autoantibody or autoantibodies against the alpha-subunit is or are present or not.

In a preferred embodiment, the term "immobilized", as used herein, means that the agent for the detection of whether an autoantibody against the beta-subunit of the gastric $H^+/K^+$-ATPase is present or not is bound to the solid phase of the carrier, preferably via a covalent bond, electrostatic interaction or via a hydrophobic interaction, the agent remaining exposed to the environment such that it is accessible for autoantibodies in a liquid sample. Various suitable carriers, for example paper, polystyrene, metal, silicone or glass surfaces, microfluidic channels, membranes, beads such as magnetic beads, chromatography column media, biochips, polyacrylamide gels and the like, are described in the literature, for example in Kim, D. and Herr, A. E. (2013), Protein immobilization techniques for microfluidic assays, Biomicrofluidics 7(4), 041501. In this way, the immobilized agent together with the insoluble carrier can be easily separated from an aqueous solution, for example by filtration, centrifugation or decanting. An immobilized agent can be reversibly or irreversibly immobilized. For example, the immobilization is reversible when the agent interacts with the carrier via an ionic interaction, which can be masked by addition of a high concentration of a salt, or when the agent is bound via a cleavable covalent bond such as a disulfide bridge, which can be cleaved by addition of thiol-comprising reagents. In contrast, the immobilization is irreversible when the agent is attached to the carrier via a covalent bond which cannot be cleaved in aqueous solution, for example a bond which is formed by reaction of an epoxy group and an amino group, as is frequently used for binding lysine side chains to affinity columns. The agent, preferably a polypeptide, can be immobilized indirectly, for example by immobilization of an antibody or some other entity having affinity for the agent, followed by the formation of a complex with the effect that the agent-antibody complex is immobilized. Said agent can also be immobilized directly, i.e. for coating the carrier in direct contact. Various options for immobilization are described in the literature, for example in Kim. D. and Herr, A. E. (2013), Protein immobilization techniques for microfluidic assays, Biomicrofluidics 7(4), 041501.

The beta-subunit of the gastric $H^+/K^+$-ATPase is preferably the amino acid sequence represented with the UniProtKB sequence entry P51164 or in SEQ ID NO: 7, more preferably the amino acid sequence represented by SEQ ID NO: 3, the latter representing the extracellular domain which does not comprise the transmembrane domain, even more preferably the fragment represented in SEQ ID NO: 5. According to the invention, variants thereof can be used. In this application, all the cited database codes stand for the Uniprot database or other databases, more precisely for the version thereof on the filing date of said application or its earliest priority application. It is particularly preferred that SEQ ID NO: 3 or a variant thereof is used in the absence of at least one epitope from the transmembrane domain of the beta-subunit having the sequence SEQ ID NO: 4 and/or at least any epitope of the alpha-subunit, which epitope is reactive towards an autoantibody from the serum of an AIG patient, preferably any epitope of the alpha-subunit.

The alpha-subunit of the gastric $H^+/K^+$-ATPase is preferably the amino acid sequence represented by UniProtKB access number P20648 or in SEQ ID NO: 9. Intrinsic factor is preferably the amino acid sequence represented by the NCBI GenBank entry NP_005133.2 or in SEQ ID NO: 10.

In a preferred embodiment, "detecting whether an autoantibody against the beta-subunit of the gastric $H^+/K^+$-ATPase is present or not in a sample" is understood to mean that what is detected is whether the sample contains an autoantibody which is directed against the beta-subunit, but not against the alpha-subunit of the same protein. Preferably, an antibody which is directed only against the complex comprising alpha-subunit and beta-subunit is also not detected. In this connection, particular preference is given to generating a first signal indicating that the autoantibody against the beta-subunit has bound and can be distinguished from a signal which arises from a different autoantibody binding to a different autoantigen such as the alpha-subunit or to an autoantigen consisting of amino acids of the alpha- and the beta-subunits. Thus, what can be distinguished is whether an antibody specific for the beta-subunit is binding to the beta-subunit, or whether a different event has taken place, particularly the binding of an autoantibody which binds against the alpha-subunit or the complex composed of alpha-subunit and beta-subunit, but not the beta-subunit alone. In a preferred embodiment, the invention uses, instead of an agent for specific capture, an agent for the specific detection of whether an autoantibody against the beta-subunit of the gastric $H^+/K^+$-ATPase is present or not in a sample, preference being given to an agent allowing the detection of whether an autoantibody against the beta-subunit of the gastric $H^+/K^+$-ATPase is present or not in a sample. The agent for detection or the agent for specific capture can be a polypeptide or a reagent or a composition for detection or specific capture.

The detection of the autoantibody can be qualitative or quantitative. In a preferred embodiment, the term "qualitative" is understood to mean that what is merely detected is whether the antibody is present or not, but not in what concentration. In particular, there is no establishment of whether the concentration of the antibody exceeds a certain value, which yields further information about the disease in question, for example about the severity of the disease, about the development, about the success of therapy or about certain symptoms. In a preferred embodiment, the term "quantitative" is understood to mean that information going beyond that about being able to detect the antibody is provided. In particular, it is possible to determine an absolute or relative value, or at least an assignment to one of multiple defined concentration ranges.

This can be achieved by the beta-subunit or a variant thereof being used spatially separated from other antigens, preferably autoantigens or epitopes of such autoantigens, which epitopes are reactive towards autoantibodies from samples from AIG patients, especially the alpha-subunit or variants thereof. Alternatively, it is possible to detect whether an autoantibody which binds against the complex comprising alpha-subunit and beta-subunit of the gastric $H^+/K^+$-ATPase is present in the sample, and additionally whether an antibody which binds specifically against the alpha-subunit is not present in the sample. If this is namely the case, it can be concluded that an autoantibody which binds specifically against the beta-subunit is present, even though neither the beta-subunit nor a variant thereof is used for the assay. Lastly, there is also the option of immobilizing all the antibodies of the searched class, preferably IgG, that are present in the sample, followed by contacting with the beta-subunit of the gastric $H^+/K^+$-ATPase, which either is itself labelled or can be detected via a labelled ligand, preferably a labelled antibody.

For the assessment of whether a patient has an increased risk of suffering from or contracting AIG and/or PA, preference is given to using solely the presence or absence of autoantibodies against the beta-subunit to indicate whether this is the case. By contrast, no attention is paid to the detection of autoantibodies against the alpha-subunit, because it does not indicate such an increased risk.

In a preferred embodiment, the "agent for the specific capture of an autoantibody against the beta-subunit of the gastric $H^+/K^+$-ATPase" is understood to mean an agent which can capture an autoantibody against the beta-subunit of the gastric $H^+/K^+$-ATPase, but can capture other antibodies, preferably autoantibodies, particularly against the alpha-subunit, less efficiently, most preferably not at all or to a non-detectable extent, with the result that they remain uncaptured in the sample in a detection method according to the invention when contacting the agent or agent-comprising carrier with the sample. Preferably, the agent for the specific capture of an autoantibody against the beta-subunit of the gastric $H^+/K^+$-ATPase binds specifically to an autoantibody against the beta-subunit from a sample from an AIG patient. In a preferred embodiment, among all autoantibodies again the $H^+/K^+$-ATPase only those binding against the beta subunit, preferably in particular not those binding against the alpha subunit, are used or used as Marker for diagnosing AIG. This autoantibody or these autoantibodies serve as the only autoantibody marker for the diagnosis in line with the present invention. Preferably, epitopes from or derived from the alpha subunit, to which autoantibodies against the alpha subunit, but not autoantibodies against the beta subunit bind, are absent.

In a particularly preferred embodiment, the term "bind specifically", as used herein, in the case of an antibody means that said antibody binds against the relevant antigen in a binding reaction characterized by a dissociation constant which is $1\times10^{-5}$ M, more preferably $1\times10^{-7}$ M, more preferably $1\times10^{-8}$ M, more preferably $1\times10^{-5}$ M, more preferably $1\times10^{-10}$ M, more preferably $1\times10^{-11}$ M, more preferably $1\times10^{-12}$ M or a stronger binding reaction. Preferably, the dissociation constant is, in this connection, measured by surface plasmon resonance using a Biacore instrument at 25° C. and in PBS buffer at pH 7 and calculated using the software provided by the manufacturer.

In a preferred embodiment, the term "diagnosis", as used herein, is understood to mean a procedure which yields information which supports the assessment, or allows it in the first place, of whether a subject is suffering from a disease or has a higher probability of suffering from a disease than an average person or suffered in the past or will suffer in the future, or whether a disease is progressing or how it will develop in the future, or for assessing whether a certain treatment is taking effect. Preferably prior to the diagnosis it is unknown whether or not the subject to be diagnosed suffers from the disease.

Preferably, for the diagnosis or to support the diagnosis, it is sufficient to merely detect whether the antibody is present, it being possible to determine whether detectable concentrations of the antibody are present in the sample. In a preferred embodiment, what is determined is whether the relative concentration of the antibody is higher in a patient to be diagnosed than in an average healthy person. What can be determined is whether the concentration is higher by a factor of 1.1, more preferably 1.2, 1.5, 1, 2, 5, 10, 20, 25, 50, 100, 200, 500, 1000, 10 000 or 100 000, than in a sample from an average healthy person. The higher concentration supports the diagnosis that a patient from whom the sample originates is suffering from AIG or indicates that the patient has an increased probability of suffering from AIG.

The method according to the invention or the use according to the invention is preferably effected in vitro.

A person skilled in the art understands that such a diagnosis generally does not by itself allow a comprehensive diagnosis, but that further aspects must be taken into consideration, for example further parameters to be determined in a sample, medical history, clinical symptoms, anamnesis or the results of imaging methods. Said person further understands that the value of the method according to the invention can consist in it being possible to carry out an indirect diagnosis or differential diagnosis in which the exclusion of a disease indicates that the patient is suffering from a different disease with similar symptoms. In a preferred embodiment, products according to the invention, such as carriers or kits, or methods according to the invention serve for the differentiation between a gastritis caused by autoimmunity and a gastritis caused by bacteria or by medicaments or for the diagnosis of a disease from the group comprising AIG, pernicious anaemia, atrophic body gastritis or vitamin B12 deficiency.

In the event of antibodies being detected, the sample to be investigated is a sample comprising a representative set of antibodies from the patient, who is preferably a mammal, even more preferably a human. Preferably, said sample is selected from the group comprising serum, plasma, serum and CSF.

It is possible to carry out the teaching according to the invention not only by using the wild-type sequences of the specified polypeptides or the reference sequences, as specified here in the form of SEQ ID NO:, collectively referred to henceforth as "full-length polypeptide", or database codes or in some other way, possibly implicitly, but also by using variants of said sequences.

In a particularly preferred embodiment, the term "variant", as used herein, means, in this connection, at least one fragment of the full-length polypeptide which is truncated at the C-terminal and/or N-terminal end by one or more than one amino acid compared to the full-length polypeptide. Such a fragment can contain a length of 5, 6, 7, 8, 10, 12, 15, 20, 25, 50, 75, 100, 150 or 200 successive amino acids from the sequence of the full-length polypeptide, preferably 10 or more.

In a further preferred embodiment, the term "variant", as used herein, encompasses not only a fragment, but also a polypeptide having amino acid sequences with, in the order of increasing preference, at least 40%, 50%, 60%, 70%, 75%, 80%, 85%, 90%, 92%, 94%, 95%, 96%, 97%, 98% or 99% sequence identity in relation to the full-length polypeptide or in relation to the fragment thereof, with no deletion or non-conservative substitution of an amino acid essential for biological activity, i.e. the ability of an antigen to bind to an antibody specific for the full-length polypeptide antigen. The related art discloses methods for establishing the sequence identity of amino acid sequences, for example in Arthur Lesk (2008). Introduction to bioinformatics, Oxford University Press, 2008, third edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G.

(2007). Clustal W and Clustal X version 2.0. Bioinformatics, 23, 2947-2948) is used to this end with use of the standard settings.

In addition, a polypeptide used according to the invention or a variant thereof can have chemical modifications, for example isotope label, covalent modifications such as glycosylation, phosphorylation, acetylation, decarboxylation, citrullination, methylation, hydroxylation, etc. In a particularly preferred embodiment, a polypeptide which is used for the detection of an autoantibody against the beta-subunit or used some other way according to the invention and which comprises the beta-subunit or a variant thereof is glycosylated. The glycosylation is preferably accomplished by expression in a cell capable of glycosylation, preferably a mammalian or insect cell, more preferably a mammalian cell.

Variants can also be fusion proteins with amino acids or other known polypeptides or variants thereof, preferably with a purification tag, even more preferably from the group comprising His tag, thioredoxin, maltose-binding protein, streptavidin, glutathione S-transferase or a variant thereof, and be or comprise active parts or domains, preferably with a sequence identity of at least 70%, 75%, 80%, 85%, 90%, 92%, 94%, 95%, 96%, 97%, 98% or 99% in relation to the full-length polypeptide. In a preferred embodiment, the term "active parts or domains" is understood to mean a fragment of the full-length polypeptide or a variant which, in both cases, retains at least some of the biological activity of the full-length polypeptide.

It is essential that the variant of the full-length polypeptide has biological activity. In a preferred embodiment, biological activity is the capability of an agent, preferably polypeptide, to capture an autoantibody against the beta-subunit or to bind thereto, preferably bind specifically, which autoantibody occurs in samples from patients who have contracted AIG. The autoantibody from such samples can be obtained as reference for tests. Variants of a secondary antibody serving for the detection of a specifically captured antibody are all molecules which have the same binding specificity as the secondary antibody, preferably the capability of binding against all antibodies of human class IgG. For example, they encompass fragments and derivatives of the secondary antibody.

When producing variants or assessing whether they may exhibit biological activity, a person skilled in the art can orientate himself/herself to the work by da Silva et al. (da Silva, H. D., Gleeson, P. A., Toh, B. H., Van Driel, I. R. and Carbone, F. R. (1999) Identification of a gastritogenic epitope of the H/K ATPase beta-subunit, Immunology 1999, 96, 145-151). They identified SEQ ID NO: 6 as the peptide comprising the immunodominant epitope. This means that the homologous sequence from the human protein represented in SEQ ID NO: 5 contains the human epitope. By means of sequence alignments with further mammalian homologues, for example from pig, cattle, primates, goat and others, a person skilled in the art can easily predict reactive variants. By means of mutations and further truncations, a person skilled in the art can generate further variants. Carried out by means of ELISA, as in the examples, said person can confirm that biological activity is preserved.

At the same time, a polypeptide or a variant thereof does not bind, or only binds to a slight extent, against antibodies against the alpha-subunit, preferably the immunodominant epitope thereof, as described in SEQ ID NO: 8. Homologous epitopes from further homologous mammalian enzymes can be gathered from Nishio et al. and taken into consideration for the design of variants by a person skilled in the art (Nishio, A., Hosono, M., Watanabe, Y., Sakai, M., Okuma, M. and Masuda, T. (1994) Gastroenterology 107, 1408-1414). Preferably, the binding constant of autoantibodies against the beta-subunit, as occur in a sample from a patient, is at least 10, preferably 100, more preferably 1000, more preferably 10 000, more preferably 100 000, even more preferably 1 000 000, even more preferably 10 000 000, times lower—and the strength of the binding reaction accordingly higher—than the binding constant of autoantibodies against the alpha-subunit, as occur in a sample from a patient. The binding constant characterizes, then, the strength of binding of the particular autoantibody against the variant, more precisely a mixture of autoantibodies, as occur in a sample. The binding constant is, in this connection, preferably measured by means of Biacore in PBS buffer at 25° C. For example, the binding constant can be $10^{-10}$ M in the case of the binding of autoantibodies against the beta-subunit from a sample, whereas the binding constant of the same autoantibodies against the alpha-subunit from the sample is $10^{-6}$ M. The first binding constant is thus 10 000 times lower than the second one. This means that autoantibodies against the beta-subunit bind distinctly more strongly to the polypeptide or the variant than autoantibodies against the alpha-subunit. If the polypeptide or the variant is used according to the invention, only autoantibodies against the beta-subunit are thus bound and detected, but not antibodies against the alpha-subunit.

In a preferred embodiment, the term "autoantibody", as used herein, is understood to mean an antibody which binds specifically to a structure, preferably an autoantigen, from the organism which produces said antibody. Such an autoantibody has a constant region, as is had by other antibodies of the same class from the same organism. Particularly preferably, the autoantibody is a mammalian autoantibody, even more preferably a human autoantibody, even more preferably a human autoantibody of class IgG. The variable domain is capable of binding specifically against the autoantigen. Preferably, the autoantigen is an epitope derived from or contained in the beta-subunit, preferably SEQ ID NO: 5 or a variant thereof.

In a preferred embodiment, the agent for capture is an isolated and/or purified polypeptide, which is particularly preferably recombinant. In this connection, an "isolated" polypeptide can be understood to mean that the polypeptide has been removed from its natural environment or the environment in which it had been expressed. In a preferred embodiment, a "purified" polypeptide is understood to mean a polypeptide which has been enriched with respect to the concentration and/or purity in its natural environment by using chromatographic methods, preferably selected from the group comprising affinity chromatography, gel-filtration chromatography and ion-exchange chromatography. In a particularly preferred embodiment, a polypeptide is purified when it has a purity of at least 40%, 50%, 60%, 70%, 80%, 90%, 95%, 98%, 990/or 99.5%, which can be estimated visually or, preferably, by measurement of band intensities on an SDS-PAGE gel after Coomassie staining.

A polypeptide can be provided in the form of a tissue or a cell, preferably a recombinant tissue or a recombinant cell. The cell is preferably a eukaryotic cell, more preferably an insect, plant or mammalian cell, even more preferably a mammalian cell such as a human cell, most preferably an HEK293 cell.

A polypeptide as agent can be provided in folded form or in unfolded form and is preferably folded. Preferably, folding is measured by means of CD spectroscopy in a buffer which allows the measurement and in which the protein can assume its three-dimensional folding (see, for example, Banaszak, L. J. (2008), Foundations of Structural Biology, Academics Press, or Teng, Q. (2013), Structural Biology: Practical Applications, Springer), for example in 10 mM sodium phosphate buffer at pH 7. Preferably, the protein assumes folding recognized by an antibody to be detected.

In a preferred embodiment, an antibody is, after capture, detected by a method from the group comprising the measurement of immunodiffusion, immunoelectrophoresis, light scattering, agglutination, radioactivity, enzymatic activity, (electro)chemiluminescence and immunofluorescence. In the case of a detection by radioactivity, enzymatic activity, (electro)chemiluminescence and immunofluorescence, it is possible to use a detectable label. Said label is preferably attached to a secondary antibody which binds to the antibody to be detected. Detection methods are, for example, described in Zane, H. D. (2001), Immunology—Theoretical & Practical Concepts in Laboratory Medicine, W. B. Saunders Company, particularly in chapter 14.

The invention provides a kit comprising the carrier according to the invention, the kit comprising one reagent or more than one reagent, preferably all the reagents, from the group comprising a wash solution, at least one calibrator solution, an antibody against the beta-subunit of the gastric $H^+/K^+$-ATPase, and an agent for the detection of the autoantibody, preferably a secondary antibody, even more preferably a secondary antibody against IgG antibodies, or the beta-subunit of the gastric $H^+/K^+$-ATPase or a variant thereof, preferably having a detectable label, a dilution buffer for the dilution of the sample, a positive control, a chemiluminescence trigger solution and a substrate capable of chemiluminescence. Instead of the chemiluminescence trigger solution and the substrate capable of chemiluminescence, a chromogenic solution e.g. for an ELISA can also be contained.

The autoantibody detection can be quantitative or semi-quantitative, preferably semi-quantitative. In a preferred embodiment, it is understood that "semi-quantitative" means that what is determined is whether the measurement result lies above a certain threshold value, for example 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 RU/ml. The value in RU/ml is, in this connection, preferably measured by means of ELISA (EA 1361-9601 G) from EUROIMMUN Medizinische Labordiagnostika AG.

A calibrator solution, as used in the method according to the invention, is understood to mean a solution comprising a defined amount of an antibody which binds against the same antigen as the autoantibody to be detected and preferably belongs to the same IgG class as the antibody to be detected, the antigen preferably being the beta-subunit. The calibrator may comprise an amount of the antibody which is known in absolute or relative terms. For example, one calibrator solution may comprise ten times as much antibody as another one. The antibody present in a defined amount can be an autoantibody from a sample or a recombinant monoclonal antibody. Preferably, more than two, preferably 3, 4, 5 or 6, calibrator solutions having to different concentrations of the antibody are placed into the kit or used according to the invention, in particular investigated in parallel to a sample, with the result that a calibration curve for the semi-quantitative or quantitative determination of the autoantibody against the beta-subunit can be plotted. In a preferred embodiment, the calibrator comprises an autoantibody or antibody against the beta subunit of the gastric $H^+/K^+$-ATPase, preferably less or no detectable amounts of or no autoantibody or antibody against the alpha subunit.

According to the invention, a monoclonal antibody or isolated autoantibody which binds specifically against the beta-subunit of the gastric $H^+/K^+$-ATPase is used particularly preferably in recombinant, isolated and/or purified form, most preferably against SEQ ID NO: 5. Such an antibody can serve as positive control for methods according to the invention and also as reagent for the immobilization of the beta-subunit or as reagent for competitive assay formats, for which it can optionally have a detectable label.

In a preferred embodiment, the captured autoantibody is detected by means of chemiluminescence. For this purpose, the autoantibody can be contacted with a ligand which is capable of chemiluminescence and which binds to the autoantibody. A ligand capable of chemiluminescence can be a secondary antibody which binds to the constant domain of the autoantibody or can be the beta-subunit of the gastric $H^+/K^+$-ATPase or a variant thereof which binds to the variable domain. The ligand capable of chemiluminescence can be an enzyme capable of chemiluminescence, for example luciferase, peroxidase, alkaline phosphatase and β-galactosidase, which can convert a substrate capable of chemiluminescence without being consumed at the same time (Kricka, L. J. (2003). Clinical applications of chemiluminescence. Analytica chimica act, 500(1): 279-286). The ligand capable of chemiluminescence can, however, also comprise an organic compound capable of chemiluminescence and without enzymatic activity, which compound emits a chemiluminescent signal in the presence of a chemiluminescence trigger solution, for example an acridinium ester (Weeks, I., Beheshti, I., McCapra, F., Campbell, A. K., Woodhead, J. S., Acridinium esters as high specific activity labels in immunoassay. Clin Chem 29: 1474-1479 (1983)) or luminol or a derivative thereof capable of chemiluminescence. This compound is consumed in the reaction.

In the case of an acridinium ester, the trigger solution used is a mixture of hydrogen peroxide and hydroxide, for example in the form of sodium hydroxide. The acridinium ester compound is, then, oxidized under alkaline conditions, and this generates light-emitting acridone. The signal is released in the form of a light flash (flash luminescence) which typically lasts 1-5 s. The short duration of the emission requires that the reaction be initiated and measured directly at the detector.

Preferably, chemiluminescence as detection method is used with a carrier which is a bead.

In a further preferred embodiment, the captured autoantibody is detected by means of ELISA. For this purpose, the agent for specific capture is immobilized in at least one well, preferably multiple wells, preferably at least 2, 4, 6, 8, 10, 12, 16, 20 or 24 wells, of an ELISA microtitre plate. A sample to be analysed is added to at least one well, and 2, 3, 4, 5 or more calibrator solutions are added to other wells. The captured antibody is then preferably detected via a secondary antibody having an enzymatically active label.

According to the invention, use is made of an agent for the specific capture of an autoantibody against the beta-subunit of the gastric $H^+/K^+$-ATPase for the calibration or for the quality-control of a medical device. In a preferred embodiment, "calibration" is understood to mean that calibrator solutions are used to obtain measurement values which confirm that the instrument is providing reliable measurement values within a required concentration range or is allowing a reliable differentiation between the presence or absence of the autoantibody in a sample. In a further preferred embodiment, "control" can mean that what is verified is that the instrument is working reliably in the sense that a sample comprising the autoantibody is actually measured as positive and a sample without the autoantibody is actually measured as negative. In a further embodiment, "control" means that what is checked is whether a batch of the agent or an instrument under given conditions has the capability, preferably still sufficient capacity, to bind the autoantibody. The medical device can be a diagnostic product such as the inventive carrier. Alternatively, it can be a therapeutic device, for example for apheresis, which likewise comprises an agent for the specific capture or detection of the autoantibody.

In a preferred embodiment, the invention provides for use of a reagent or agent or polypeptide for the detection of an autoantibody against the beta-subunit or use of a nucleic acid encoding the beta-subunit or a variant thereof or a nucleic acid which hybridizes to said nucleic acid under stringent conditions or a vector or a cell comprising the nucleic acid or the vector for the production of a kit for the diagnosis of a disease. In a preferred embodiment, a cell comprising the vector, and preferably not comprising a vector encoding the alpha-subunit or an epitope or a variant thereof, is provided and cultured under conditions allowing the expression of the nucleic acid, followed by isolation and/or purification of the expression product, followed by use of the expression product as agent for the specific capture of an antibody in a method or product according to the present invention.

In a preferred embodiment, the present invention provides an apparatus for the analysis of a sample from a patient for the detection of an autoantibody against the beta-subunit, the detection indicating an increased probability of a disease, preferably AIG and/or PAG, the apparatus comprising:

a. a carrier comprising an agent for the specific capture of the autoantibody when a sample is contacted with the carrier,
b. a detectable agent capable of binding to the antibody when said antibody has been captured upon contacting of carrier and sample as per a., the agent being especially a labelled secondary antibody which binds to the captured antibody,
c. a detection device for the detection of the presence of the detectable agent and for the conversion of the result obtained in this connection into a signal, preferably an electrical signal, and
d. optionally a means for the receiving of the signal from the detection device and for the determination of whether the level of the signal indicates an increased probability of the disease, more precisely by comparison of the level of the signal with the level of a background or threshold signal or an inputted signal value which was generated using samples from healthy persons.

The present patent application lists novel polypeptides and/or nucleic acids. They have the following sequences:

```
SEQ ID NO: 1: spGh*-H6-ATP4B(ec)
MKHLWFFLLLVAAPRWVLSGPMHHHHHHMSQTVDPYTPDYQDQLRSPGVT

LRPDVYGEKGLEIVYNVSDNRTWADLTQTLHAFLAGYSPAAQEDSINCTS

EQYFFQESFRAPNHTKFSCKFTADMLQNCSGLADPNFGFEEGKPCFIIKM

NRIVKFLPSNGSAPRVDCAFLDQPRELGQPLQVKYYPPNGTFSLHYFPYY

GKKAQPHYSNPLVAAKLLNIPRNAEVAIVCKVMAEHVTFNNPHDPYEGKV

EFKLKIEK
```

-continued

```
SEQ ID NO: 2: H6-ATP4B(ec); sequence which is
actually present in the cell and was purified for
the examples, i.e. extracellular domain, with
N-terminal His tag
GPMHHHHHHMSQTVDPYTPDYQDQLRSPGVTLRPDVYGEKGLEIVYNVSD

NRTWADLTQTLHAFLAGYSPAAQEDSINCTSEQYFFQESFRAPNHTKFSC

KFTADMLQNCSGLADPNFGFEEGKPCFIIKMNRIVKFLPSNGSAPRVDCA

FLDQPRELGQPLQVKYYPPNGTFSLHYFPYYGKKAQPHYSNPLVAAKLLN

IPRNAEVAIVCKVMAEHVTFNNPHDPYEGKVEFKLKIEK

SEQ ID NO: 3: Extracellular domain of the
ATP4B-subunit
QTVDPYTPDYQDQLRSPGVTLRPDVYGEKGLEIVYNVSDNRTWADLTQTL

HAFLAGYSPAAQEDSINCTSEQYFFQESFRAPNHTKFSCKFTADMLQNCS

GLADPNFGFEEGKPCFIIKMNRIVKFLPSNGSAPRVDCAFLDQPRELGQP

LQVKYYPPNGTFSLHYFPYYGKKAQPHYSNPLVAAKLLNIPRNAEVAIVC

KVMAEHVTFNNPHDPYEGKVEFKLKIEK

SEQ ID NO: 4: Transmembrane domain of the
ATP4B-subunit
SLYYVAFYVVMTGLFALCLYVLM

SEQ ID NO: 5: Immunodominant epitope of the human
ATP4B-subunit homologous to that from da Silva et
al.
LLNIPRNAEVAIVCKVMAEHVTFNN

SEQ ID NO: 6: Immunodominant epitope of the murine
ATP4B-subunit as per da Silva et al.
LLNVPKNMQVSIVCKILADHVTFNN

SEQ ID NO: 7: The ATP4B-subunit amino acid
sequence represented in P51164
MAALQEKKTCGQRMEEFQRYCWNPDTGQMLGRTLSRWVWISLYYVAFYVV

MTGLFALCLYVLMQTVDPYTPDYQDQLRSPGVTLRPDVYGEKGLEIVYNV

SDNRTWADLTQTLHAFLAGYSPAAQEDSINCTSEQYFFQESFRAPNHTKF

SCKFTADMLQNCSGLADPNFGFEEGKPCFIIKMNRIVKFLPSNGSAPRVD

CAFLDQPRELGQPLQVKYYPPNGTFSLHYFPYYGKKAQPHYSNPLVAAKL

LNIPRNAEVAIVCKVMAEHVTFNNPHDPYEGKVEFKLKIEK

SEQ ID NO: 8: Immunodominant epitope of the murine
ATP4A-subunit as per Nishio et al.
PLLCVGLRAQWEDHHLQDL
```

SEQ ID NO: 9: Alpha-subunit of the gastric $H^+/K^+$-ATPase, as represented in UniProtKB access number P20648

```
MGKAENYELYSVELGPGPGGDMAAKMSKKKKAGGGGGKRKEKLENMKKEM

EINDHQLSVAELEQKYQTSATKGLSASLAAELLLRDGPNALRPPRGTPEY

VKFARQLAGGLQCLMWVAAAICLIAFAIQASEGDLTTDDNLYLAIALIAV

VVVTGCFGYYQEFKSTNIIASFKNLVPQQATVIRDGDKFQINADQLVVGD

LVEMKGGDRVPADIRILAAQGCKVDNSSLTGESEPQTRSPECTHESPLET

RNIAFFSTMCLEGTVQGLVVNTGDRTIIGRIASLASGVENEKTPIAIEIE

HFVDIIAGLAILFGATFFIVAMCIGYTFLRAMVFFMAIVVAYVPEGLLAT

VTVCLSLTAKRLASKNCVVKNLEAVETLGSTSVICSDKTGTLTQNRMTVS

HLWFDNHIHTADTTEDQSGQTFDQSSETWRALCRVLTLCNRAAFKSGQDA

VPVPKRIVIGDASETALLKFSELTLGNAMGYRDRFPKVCEIPFNSTNKFQ
```

-continued

LSIHTLEDPRDPRHLLVMKGAPERVLERCSSILIKGQELPLDEQWREAFQ

TAYLSLGGLGERVLGFCQLYLNEKDYPPGYAFDVEAMNFPSSGLCFAGLV

SMIDPPRATVPDAVLKCRTAGIRVIMVTGDHPITAKAIAASVGIISEGSE

TVEDIAARLRVPVDQVNRKDARACVINGMQLKDMDPSELVEALRTHPEMV

FARTSPQQKLVIVESCQRLGAIVAVTGDGVNDSPALKKADIGVAMGIAGS

DAAKNAADMILLDDNFASIVTGVEQGRLIFDNLKKSIAYTLTKNIPELTP

YLIYITVSVPLPLGCITILFIELCTDIFPSVSLAYEKAESDIMHLRPRNP

KRDRLVNEPLAAYSYFQIGAIQSFAGFTDYFTAMAQEGWFPLLCVGLRAQ

WEDHHLQDLQDSYGQEWTFGQRLYQQYTCYTVFFISIEVCQIADVLIRKT

RRLSAFQQGFFRNKILVIAIVFQVCIGCFLCYCPGMPNIFNFMPIRFQWW

LVPLPYGILIFVYDEIRKLGVRCCPGSWWDQELYY

SEQ ID NO: 10: Intrinsic factor, as represented in NCBI Genbank entry NP_005133.2

MAWFALYLLSLLWATAGTSTQTQSSCSVPSAQEPLVNGIQVLMENSVTSS

AYPNPSILIAMNLAGAYNLKAQKLLTYQLMSSDNNDLTIGQLGLTIMALT

SSCRDPGDKVSILQRQMENWAPSSPNAEASAFYGPSLAILALCQKNSEAT

LPIAVRFAKTLLANSSPFNVDTGAMATLALTCMYNKIPVGSEEGYRSLFG

QVLKDIVEKISMKIKDNGIIGDIYSTGLAMQALSVTPEPSKKEWNCKKTT

DMILNEIKQGKFHNPMSAIQILPSLKGKTYLDVPQVTCSPDHEVQPTLPS

NPGPGPTSASNITVIYTINNQLRGVELLFNETINVSVKSGSVLLVVLEEA

QRKNPMFKFETTMTSWGLVVSSINNIAENVNHKTYWQFLSGVTPLNEGVA

DYIPFNHEHITANFTQY

SEQ ID NO: 11: cDNA encoding the ATP4A-subunit ligated into the vector pTriEx
[Only present in the sequence listings]

SEQ ID NO: 12: cDNA encoding the ATP4B-subunit ligated into the vector pTriEx
[Only present in the sequence listings]

The invention is elucidated below on the basis of exemplary embodiments with reference to the figures. The embodiments described are merely exemplary in every respect and not to be understood as limiting, and various combinations of the cited to features are encompassed by the scope of the invention.

FIG. 1 shows a Coomassie-stained polyacrylamide gel, on which, to the right of the marker, 1 μg of the purified extracellular domain of the beta-subunit of the gastric $H^+/K^+$-ATPase with N-terminal His tag in a DTT-reduced state and, to the right thereof, the same in a non-reduced state have been resolved.

Figure 2:
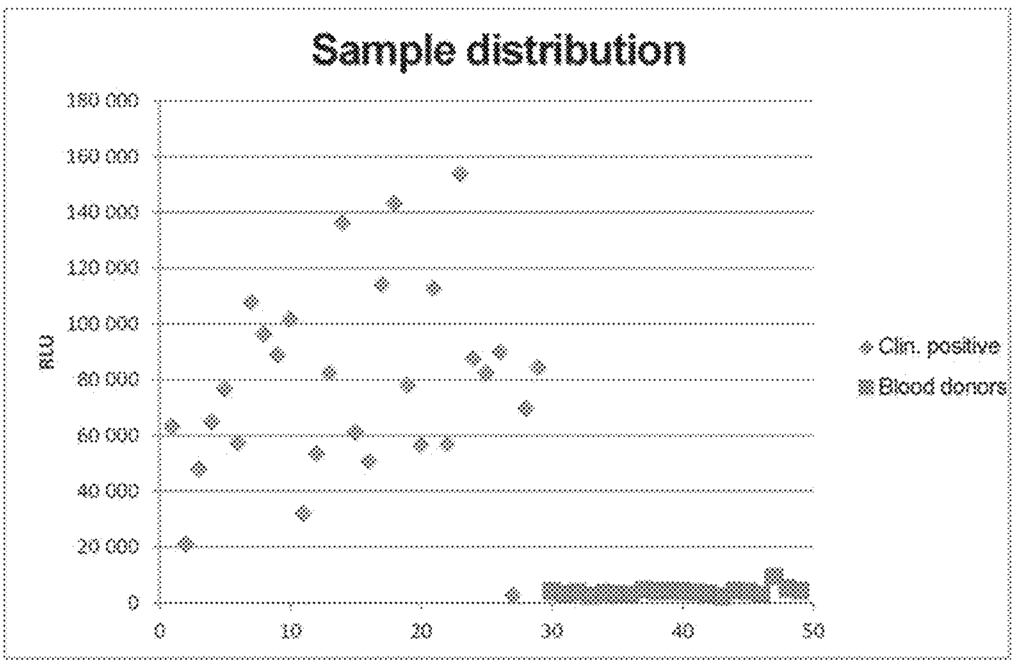
FIG. 2 shows the sample distribution in relation to the data shown in Example 3 (sensitivity) and Table 4. The y-axis shows the signal in RLU, and each number of the X-axis stands for a patient suffering from AIG (1-29) or for a healthy blood donor (starting from 30).

FIG. 2 shows the sample distribution in relation to the data shown in Example 3 (sensitivity) and Table 4. The y-axis shows the signal in RLU, and each number of the X-axis stands for a patient suffering from AIG (1-29) or for a healthy blood donor (starting from 30).

EXAMPLES

Sensitivity was investigated by using sera from patients for whom the diagnosis of AIG was made. On the other hand, specificity was investigated by using sera from clinically normal blood donors for whom it can be assumed that they do not suffer from AIG.

Example 1: Determination of the Sensitivity of a Detection by Means of the Beta-Subunit of the Gastric $H^+/K^+$-ATPase as Antigen Using Immunofluorescence and ELISA The human cDNA described by Genbank access number BC167780 and encoding the ATP4A-subunit was ligated into the vector pTriEx (yielding SEQ ID NO: 11). The human cDNA described by Genbank access number BC029059 and encoding the ATP4B-subunit was likewise ligated into the vector pTriEx (yielding SEQ ID NO: 12).

Production of Substrates for Indirect Immunofluorescence

HEK293 cells cultured on glass slides in D-MEM comprising an addition of 10% (v/v) foetal calf serum were transfected with the plasmid DNA encoding ATP4A or ATP4B, individually and in combination, and additionally, for the production of a negative control, with the empty pTriEx vector by means of 25 kDa linear polyethyleneimine and fixed after 48 hours. For the fixation, the glass slides with the adherent cells were first washed with PBS and then fixed alternately with 1.8% formalin solution in PBS for 5 minutes and in acetone at room temperature for 10 minutes. Finally, a wash and blocking step was carried out in PBS comprising an addition of 1% (w/v) BSA (PBS (1% w/v BSA)) at room temperature for 5 minutes.

All the incubation steps were carried out at room temperature.

Immunofluorescence Analysis

The serum or plasma samples to be analysed were incubated on the substrate in a 1:10 dilution in PBS (1% w/v BSA) for 30 minutes. Thereafter, the substrates were washed in PBS (0.2% v/v Tween 20) for 5 minutes. Bound human immunoglobulin of class IgG was detected using fluorescein-labelled anti-human IgG in a 30-minute incubation step. Excess conjugate was removed with PBS (0.2% v/v Tween 20) for 5 minutes before evaluation on an immunofluorescence microscope. Immunofluorescence was evaluated semi-quantitatively by indication of the intensity of the specific fluorescent signal in intensities of 0 (no fluorescence), trace (borderline signal), 1 (faintly positive), 2, 3 and 4 (highly positive).

Purification of the Extracellular Domain of ATP4B (SEQ ID NO: 2) Expressed Using Vector pTriEx-1 in HEK293 Cells:

HEK293 cells cultured in D-MEM comprising an addition of 10% (v/v) foetal calf serum were transfected with the plasmid DNA encoding spGh*-H6-ATP4B(ec) by means of 25 kDa linear polyethyleneimine. On day 5 after transfection, the cell culture supernatant was removed, clarified by centrifugation, and used for the purification of the recombinant protein by means of immobilized metal-chelate affinity chromatography (IMAC) using standard protocols. The purified protein stained with Ponceau S is shown in FIG. 1.

ELISA Analysis:

The experiments were carried out as described in Dähnrich et al. (2013) Development of a standardized ELISA for the determination of autoantibodies against human M-type phospholipase A2 receptor in primary membranous nephropathy, Clinica Chimica Acta 421, 213-218, with the exception of the extracellular domain of ATP4B (SEQ ID NO: 2) being used as the antigen.

In brief, microtitre plates (Nunc, Germany) were coated overnight with 0.7 μg/ml antigen in PBS at 4° C. and washed three times with wash buffer (0.05% (w/v) Tween 20 in PBS). Non-specific binding sites were blocked by means of a one-hour incubation with 0.1% casein (w/v) in PBS.

Samples of human serum were diluted 1:100 in sample buffer (0.05% (w/v) Tween 20, 1% (w/v) casein in PBS) and incubated for 30 minutes, followed by three wash steps with wash buffer. In addition to two positive samples from clinically characterized patients, seven further samples from patients were investigated.

Bound antibodies were detected by means of a 30-minute incubation with anti-human IgG HRP conjugate (EUROIMMUN, Germany) which was diluted 1:1000 in sample buffer. Thereafter, washing was carried out as described above, followed by addition of 3,3',5,5'-tetramethylbenzidine (EUROIMMUN Medizinische Labordiagnostika AG) and a 15-minute incubation. All the incubation steps were carried out at room temperature.

Optical density (OD) was measured at 450 nm using an automatic spectrophotometer (Spectra Mini, Tecan, Crailsheim, Germany). The cut-off was ascertained by ROC curve analysis (maximum sum of sensitivity plus specificity).

For comparison, the assay was also carried out using the conventional anti-PCA ELISA (IgG) (EUROIMMUN Medizinische Labordiagnostika AG, order number EA 1361 G).

Results:

TABLE 1

Result of the investigation of sensitivity by means of ELISA and IFT

| | | ELISA | | | IFT | | | |
|---|---|---|---|---|---|---|---|---|
| | | Anti-PCA ELISA (IgG) Cut-off: 20 U/ml | | Anti-ATP4B ELISA (IgG) (serum 1:101) 30% sucrose/ 0.1% casein Normalized | ATP-4A + ATP-4B | ATP-4A | ATP-4B | IFT Total result |
| | | | | | Formalin-fixed | | | |
| | Sample | OD | RU/ml | OD* | Sample dilution 1:10 | | | |
| AIG patients (n = 29) | 01122017-27 | 0.842 | 119 | 0.011 | 0 | 0 | 0 | Neg. |
| | 01122017-2 | 0.597 | 71 | 0.369 | 3 | 0 | 3 | Pos. |
| | 01122017-11 | 0.491 | 50 | 0.468 | 2 | 0 | 2 | Pos. |
| | 01122017-3 | 0.699 | 91 | 0.749 | 2.5 | 0 | 3 | Pos. |
| | 01122017-22 | 0.873 | 125 | 0.821 | 2.5 | 0 | 2.5 | Pos. |
| | 01122017-12 | 0.369 | 26 | 0.828 | 2 | 0 | 2 | Pos. |
| | 01122017-20 | 0.411 | 34 | 0.862 | 3 | 0 | 3 | Pos. |
| | 01122017-16 | 1.307 | >200 | 0.894 | 2 | 0 | 2 | Pos. |
| | 01122017-4 | 0.512 | 54 | 0.914 | 3 | 0 | 3 | Pos. |
| | 01122017-28 | 0.694 | 90 | 0.970 | 2.5 | 0 | 1.5 | Pos. |
| | 01122017-15 | 1.566 | >200 | 0.986 | 3 | 1 | 3 | Pos. |
| | 01122017-6 | 1.545 | >200 | 0.988 | 3 | 0 | 3 | Pos. |
| | 01122017-1 | 0.923 | 135 | 0.994 | 2.5 | 0 | 2.5 | Pos. |
| | 01122017-25 | 0.989 | 148 | 1.126 | 3 | 0 | 3 | Pos. |
| | 01122017-19 | 0.792 | 109 | 1.139 | 2.5 | 0.5 | 3 | Pos. |
| | 01122017-29 | 1.004 | 151 | 1.145 | 2.5 | 0 | 3 | Pos. |
| | 01122017-24 | 0.795 | 110 | 1.171 | 3 | 0 | 3 | Pos. |
| | 01122017-13 | 1.622 | >200 | 1.193 | 2 | 0 | 2 | Pos. |
| | 01122017-9 | 1.386 | >200 | 1.195 | 2 | 0 | 2 | Pos. |
| | 01122017-5 | 0.855 | 121 | 1.221 | 3 | 0 | 3 | Pos. |
| | 01122017-26 | 1.512 | >200 | 1.228 | 2.5 | 0.5 | 3 | Pos. |
| | 01122017-8 | 1.195 | 188 | 1.259 | 3 | 0 | 3 | Pos. |
| | 01122017-10 | 1.229 | 195 | 1.269 | 3 | 0 | 3 | Pos. |
| | 01122017-7 | 1.132 | 176 | 1.346 | 3 | 0 | 3 | Pos. |
| | 01122017-21 | 1.506 | >200 | 1.378 | 3 | 0 | 3 | Pos. |
| | 01122017-17 | 1.840 | >200 | 1.391 | 2 | 0 | 2 | Pos. |
| | 01122017-14 | 1.259 | >200 | 1.449 | 3 | 0 | 3 | Pos. |
| | 01122017-18 | 1.889 | >200 | 1.488 | 2.5 | 1 | 3 | Pos. |
| | 01122017-23 | 1.535 | >200 | 1.551 | 2 | 0 | 2 | Pos. |

*Normalized to functional controls, qualitative evaluation via cut-off from ROC analysis (0.284)

Example 2: Determination of the Specificity of a Detection by Means of the Beta-Subunit of the Gastric $H^+/K^+$-ATPase as Antigen Using ELISA in Comparison with the Conventional Assay (Related Art)

The experiments were carried out as described in Example 1, with the exception of use of sera from clinically normal blood donors.

Result:

TABLE 2

Result of the investigation of specificity by means of ELISA with comparison of a conventional anti-PCA ELISA and the inventive method using samples from blood donors

| | | | | Conventional assay:anti-PCA ELISA 1:201 | | Inventive:anti-ATP4B(ec) ELISA 1:101 PB of 15.11.2018 | |
|---|---|---|---|---|---|---|---|
| | | | | E170731AD | | | U/ml |
| | Sample | Age | Sex | OD | U/ml | OD | (simulated) |
| Blood donor 2014-II | BS 2014-II-2 | 21 | M | 0.054 | 3 | 0.015 | <Min |
| | BS 2014-II-15 | 29 | M | 0.029 | <Min | 0.025 | <Min |
| | BS 2014-II-16 | 24 | F | 0.018 | <Min | 0.015 | <Min |
| | BS 2014-II-18 | 23 | M | 0.069 | 4 | 0.017 | <Min |
| | BS 2014-II-19 | 24 | M | 0.021 | <Min | 0.014 | <Min |
| | BS 2014-II-20 | 20 | F | 0.027 | <Min | 0.021 | <Min |
| | BS 2014-II-21 | 62 | M | 0.022 | <Min | 0.012 | <Min |
| | BS 2014-II-25 | 28 | F | 0.456 | 50 | 0.585 | 85 |
| | BS 2014-II-27 | 27 | M | 0.103 | 6 | 0.008 | <Min |
| | BS 2014-II-31 | 42 | M | 0.018 | <Min | 0.016 | <Min |
| | BS 2014-II-34 | 51 | M | 0.022 | <Min | 0.017 | <Min |
| | BS 2014-II-35 | 24 | M | 0.047 | 2 | 0.009 | <Min |
| | BS 2014-II-36 | 28 | M | 0.052 | 3 | 0.014 | <Min |
| | BS 2014-II-37 | 52 | M | 0.072 | 4 | 0.016 | <Min |
| | BS 2014-II-38 | 26 | F | 0.013 | <Min | 0.022 | <Min |
| | BS 2014-II-39 | 25 | M | 0.015 | <Min | 0.014 | <Min |
| | BS 2014-II-40 | 35 | M | 0.022 | <Min | 0.015 | <Min |
| | BS 2014-II-41 | 44 | M | 0.169 | 11 | 0.020 | <Min |
| | BS 2014-II-42 | 45 | M | 0.197 | 13 | 0.013 | <Min |
| | BS 2014-II-44 | 29 | F | 0.245 | 16 | 0.020 | <Min |
| | BS 2014-II-45 | 53 | M | 0.011 | <Min | 0.010 | <Min |
| | BS 2014-II-46 | 23 | M | 0.010 | <Min | 0.033 | <Min |
| | BS 2014-II-47 | 24 | M | 0.044 | 2 | 0.009 | <Min |
| | BS 2014-II-48 | 21 | M | 0.031 | <Min | 0.018 | <Min |
| | BS 2014-II-50 | 21 | M | 0.122 | 7 | 0.008 | <Min |
| | BS 2014-II-52 | 29 | F | 0.082 | 5 | 0.016 | <Min |
| | BS 2014-II-54 | 59 | M | 0.009 | <Min | 0.009 | <Min |
| | BS 2014-II-55 | 43 | F | 0.026 | <Min | 0.006 | <Min |
| | BS 2014-II-57 | 20 | M | 0.064 | 3 | 0.019 | <Min |
| | BS 2014-II-58 | 44 | F | 0.046 | 2 | 0.012 | <Min |
| | BS 2014-II-59 | 26 | M | 0.080 | 5 | 0.011 | <Min |
| | BS 2014-II-61 | 66 | M | 0.018 | <Min | 0.014 | <Min |
| | BS 2014-II-63 | 21 | F | 0.036 | <Min | 0.013 | <Min |
| | BS 2014-II-64 | 21 | F | 0.124 | 8 | 0.015 | <Min |
| | BS 2014-II-65 | 46 | M | 0.037 | <Min | 0.008 | <Min |
| | BS 2014-II-66 | 28 | M | 0.133 | 8 | 0.014 | <Min |
| | BS 2014-II-67 | 37 | M | 0.010 | <Min | 0.010 | <Min |
| | BS 2014-II-68 | 25 | M | 0.037 | <Min | 0.011 | <Min |
| | BS 2014-II-69 | 19 | M | 0.145 | 9 | 0.007 | <Min |
| | BS 2014-II-70 | 36 | M | 0.022 | <Min | 0.008 | <Min |
| | BS 2014-II-71 | 34 | M | 0.153 | 10 | 0.016 | <Min |
| | BS 2014-II-72 | 35 | F | 0.055 | 3 | 0.015 | <Min |
| | BS 2014-II-73 | 24 | F | 0.060 | 3 | 0.013 | <Min |
| | BS 2014-II-74 | 41 | F | 0.070 | 4 | 0.008 | <Min |
| | BS 2014-II-75 | 44 | M | 0.016 | <Min | 0.038 | <Min |
| | BS 2014-II-76 | 50 | M | 0.092 | 5 | 0.042 | <Min |
| | BS 2014-II-77 | 44 | M | 0.037 | <Min | 0.023 | <Min |
| | BS 2014-II-78 | 46 | M | 0.618 | 81 | 0.013 | <Min |
| | BS 2014-II-79 | 20 | M | 0.361 | 31 | 0.027 | <Min |
| | BS 2014-II-80 | 26 | M | 0.038 | <Min | 0.012 | <Min |
| | BS 2014-II-201 | 49 | M | 0.115 | 7 | 0.049 | 2 |
| | BS 2014-II-204 | 64 | M | 0.029 | <Min | 0.020 | <Min |
| | BS 2014-II-205 | 55 | F | 0.066 | 4 | 0.029 | <Min |
| | BS 2014-II-206 | 58 | F | 0.050 | 2 | 0.013 | <Min |

TABLE 2-continued

Result of the investigation of specificity by means of ELISA with comparison of a conventional anti-PCA ELISA and the inventive method using samples from blood donors

| | | | | | | | |
|---|---|---|---|---|---|---|---|
| | BS 2014-II-207 | 45 | M | 0.040 | <Min | 0.126 | 8 |
| | BS 2014-II-209 | 29 | M | 0.066 | 4 | 0.010 | <Min |
| | BS 2014-II-210 | 45 | M | 0.053 | 3 | 0.017 | <Min |
| | BS 2014-II-211 | 23 | M | 0.012 | <Min | 0.009 | <Min |
| | BS 2014-II-214 | 41 | M | 0.405 | 40 | 0.271 | 18 |
| | BS 2014-II-215 | 45 | M | 0.013 | <Min | 0.015 | <Min |
| | BS 2014-II-216 | 42 | M | 0.066 | 4 | 0.024 | <Min |
| | BS 2014-II-218 | 52 | F | 0.828 | 122 | 0.014 | <Min |
| | BS 2014-II-220 | 58 | M | 0.026 | <Min | 0.018 | <Min |
| | BS 2014-II-221 | 25 | M | 0.049 | 2 | 0.013 | <Min |
| | BS 2014-II-222 | 50 | M | 0.038 | <Min | 0.010 | <Min |
| | BS 2014-II-224 | 24 | M | 0.042 | <Min | 0.013 | <Min |
| | BS 2014-II-225 | 48 | M | 0.019 | <Min | 0.017 | <Min |
| | BS 2014-II-228 | 63 | M | 0.163 | 10 | 0.012 | <Min |
| | BS 2014-II-229 | 40 | M | 0.052 | 3 | 0.014 | <Min |
| | BS 2014-II-230 | 21 | F | 0.098 | 6 | 0.018 | <Min |
| | BS 2014-II-232 | 56 | M | 0.071 | 4 | 0.009 | <Min |
| | BS 2014-II-234 | 32 | F | 0.038 | <Min | 0.012 | <Min |
| | BS 2014-II-237 | 25 | M | 0.035 | <Min | 0.009 | <Min |
| | BS 2014-II-238 | 23 | M | 0.175 | 11 | 0.008 | <Min |
| | BS 2014-II-239 | 25 | M | 0.015 | <Min | 0.013 | <Min |
| | BS 2014-II-240 | 45 | M | 0.007 | <Min | 0.011 | <Min |
| | BS 2014-II-241 | 19 | M | 0.029 | <Min | 0.009 | <Min |
| | BS 2014-II-242 | 47 | M | 0.312 | 22 | 0.016 | <Min |
| | BS 2014-II-243 | 44 | M | 0.099 | 6 | 0.028 | <Min |
| | BS 2014-II-244 | 26 | F | 0.016 | <Min | 0.009 | <Min |
| | BS 2014-II-247 | 52 | M | 0.391 | 37 | 0.019 | <Min |
| | BS 2014-II-248 | 51 | M | 0.020 | <Min | 0.011 | <Min |
| | BS 2014-II-249 | 69 | M | 0.183 | 12 | 0.007 | <Min |
| | BS 2014-II-251 | 31 | M | 0.030 | <Min | 0.025 | <Min |
| | BS 2014-II-252 | 51 | M | 0.236 | 15 | 0.007 | <Min |
| | BS 2014-II-254 | 21 | M | 0.036 | <Min | 0.019 | <Min |
| Blood | BS 2014-II-255 | 21 | M | 0.033 | <Min | 0.021 | <Min |
| donor | BS 2014-II-256 | 42 | M | 0.192 | 12 | 0.014 | <Min |
| 2014-II | BS 2014-II-257 | 30 | F | 0.033 | <Min | 0.021 | <Min |
| | BS 2014-II-259 | 27 | F | 0.136 | 8 | 0.016 | <Min |
| | BS 2014-II-262 | 44 | M | 0.049 | 2 | 0.015 | <Min |
| | BS 2014-II-263 | 22 | M | 0.106 | 6 | 0.018 | <Min |
| | BS 2014-II-264 | 24 | M | 0.026 | <Min | 0.017 | <Min |
| | BS 2014-II-266 | 26 | M | 0.025 | <Min | 0.015 | <Min |
| | BS 2014-II-268 | 64 | M | 0.019 | <Min | 0.014 | <Min |
| | BS 2014-II-269 | 59 | M | 0.093 | 6 | 0.021 | <Min |
| | BS 2014-II-270 | 20 | F | 0.026 | <Min | 0.009 | <Min |
| | BS 2014-II-274 | 21 | M | 0.044 | 2 | 0.035 | <Min |
| | BS 2014-II-275 | 54 | M | 0.043 | 2 | 0.015 | <Min |
| | BS 2014-II-276 | 33 | F | 0.067 | 4 | 0.032 | <Min |
| | | | Specificity: | | 93% | | 99% |

| | | Reference: anti-PCA ELISA E170731AD | | | New development: anti-ATP4B(ec) ELISA PB of 15.11.2018 | Sens. check (cut-off determination) | | |
|---|---|---|---|---|---|---|---|---|
| | MTP 1 | OD | U/ml | Rule card | OD | OD | Factor | MW factor |
| Functional controls | 081031-151 (2) | 0.565 | 71 | 65 | 0.922 | 0.863 | 1.068366 | |
| | 011126-10 (6) | 0.913 | 139 | 158 | 1.113 | 1.113 | 1 | 1.03418308 |

| | Calibrators PCA: E170731AD | | | | |
|---|---|---|---|---|---|
| | Actual | Nominal | ATP4B(ec) | OD | OD normalized |
| K1 | 1.228 | 1.307 | KI (defined) | 1.100 | 1.100 |
| K2 | 0.303 | 0.321 | KII (ROC) | 0.284 | 0.294 |
| K3 | 0.044 | 0.05 | KIII (MW BS*1.5) | 0.047 | |
| pK | 101 | 107 | | | |

TABLE 2-continued

Result of the investigation of specificity by means of ELISA with comparison of a conventional anti-PCA ELISA and the inventive method using samples from blood donors

| MTP 2 | | Reference: anti-PCA ELISA E170731AD OD | U/ml | Rule card | New development: anti-ATP4B(ec) ELISA PB of 15.11.2018 OD | Sens. check (cut-off determination) OD | Factor | MW factor |
|---|---|---|---|---|---|---|---|---|
| Functional controls | 081031-151 (2) | 0.545 | 67 | 65 | 0.879 | 0.863 | 1.01854 | |
| | 011126-10 (6) | 0.859 | 127 | 158 | 1.123 | 1.113 | 1.008985 | 1.01376235 |

| | Calibrators PCA: E170731AD Actual | Nominal | ATP4B(ec) | OD | OD normalized |
|---|---|---|---|---|---|
| K1 | 1.242 | 1.307 | KI (defined) | 1.100 | 1.100 |
| K2 | 0.302 | 0.321 | KII (ROC) | 0.284 | 0.288 |
| K3 | 0.043 | 0.05 | KIII (MW BS*1.5) | 0.045 | 0.046 |
| pK | 101 | 107 | | | |

Conclusion:

The results show that, with the exception of the sample from the first-mentioned patient, it is also possible to detect the autoantibody against the gastric $H^+/K^+$-ATPase in the samples from patients suffering from AIG when only the extracellular domain of the beta-subunit of the gastric $H^+/K^+$-ATPase is used as antigen.

Thus, there is consequently practically no loss of sensitivity compared to the conventional ELISA.

Using the alpha-subunit of the gastric $H^+/K^+$-ATPase, practically all the samples appear, by contrast, as false-negative.

The results of Example 2 show that it is possible to achieve a considerable specificity gain of 6% compared to the conventional assay.

It should be emphasized that the conventional ELISA already exhibits a considerable specificity of 93%. Achieving a further increase in specificity to this high level is technically challenging in diagnostics and a considerable contribution over the related art.

Specificity and diagnostic reliability as a whole are increased when the method according to the invention is used.

Example 3: Determination of the Sensitivity and Specificity of a Chemiluminescence-Based Assay for the Diagnosis of AIG by Means of Determination of Autoantibody Against ATP4B Unless otherwise described, the experiment was carried out using the same reagents as described in Example 1.

In the present ChL1A, antigen-coated magnetic beads are used as solid phase for the specific detection of autoantibodies of immunoglobulin class IgG against ATP4B. The magnetic beads were produced using tosyl-activated M-280 Dynabeads (Invitrogen, catalogue number 14203, 14204) in accordance with the instructions from the manufacturer.

The assay is carried out in an automated manner in a random access analyser (RA Analyzer 10, product no. YG 0710-0101, EUROIMMUN Medizinische Labordiagnostika AG). In the first analysis step, coated magnetic beads are incubated with diluted patient samples in sample buffer (catalogue number LL9012, EUROIMMUN Medizinische Labordiagnostika AG). If the samples are anti-ATP4B-positive, specific antibodies bind to the antigen under these conditions.

In a second analysis step, acridinium ester-labelled anti-human IgG (catalogue number LK0711-G, EUROIMMUN Medizinische Labordiagnostika AG) conjugate is added, which binds to the specific antibodies.

Thereafter, the reaction mixture is admixed with trigger solutions (catalogue numbers LL0713-1 (A) and LL0713-2 (B), EUROIMMUN), which induce a chemiluminescence reaction.

The resultant light signal is outputted in relative light units (RLU). The intensity of the light signal is proportional to the quantity of the bound antibodies.

The results are shown in Table 3. A check with 20 sera from blood donors showed a specificity of 100%; with the conventional assay, it was only 95%. Data relating to sensitivity are shown in Table 4 and FIG. 2. Sensitivity was 96.5% for 29 patients suffering from autoimmune gastritis and thus is higher than the sensitivity reported by Ma et al. based on the use of non-purified beta subunit in an ELISA assay.

TABLE 3

Specificity of the inventive assay (anti-ATP4B ELISA and anti-ATP4B ChLIA) in comparison with the conventional assay (anti-PCA ELISA):

| | | | Anti-ATP4B ELISA (IgG) (serum 1:101) Cut-off: 0.284 OD Normalized OD | Anti-ATP4B ChLIA (IgG) Cut-off: 15 203 RLU RLU | Anti-PCA ELISA (IgG) Cut-off: 20 U/ml U/ml |
|---|---|---|---|---|---|
| BS 2014-II-247 | 52 | M | 0.018 | 4148 | 37 |
| BS 2014-II-248 | 51 | M | 0.011 | 3146 | <2 |
| BS 2014-II-249 | 69 | M | 0.007 | 3821 | 12 |
| BS 2014-II-251 | 31 | M | 0.024 | 2579 | <2 |
| BS 2014-II-252 | 51 | M | 0.007 | 3712 | 15 |
| BS 2014-II-254 | 21 | M | 0.018 | 3080 | <2 |
| BS 2014-II-255 | 21 | M | 0.021 | 2997 | <2 |

TABLE 3-continued

Specificity of the inventive assay (anti-ATP4B ELISA and anti-ATP4B ChLIA) in comparison with the conventional assay (anti-PCA ELISA):

| | | | Anti-ATP4B ELISA (IgG) (serum 1:101) Cut-off: 0.284 OD Normalized OD | Anti-ATP4B ChLIA (IgG) Cut-off: 15 203 RLU RLU | Anti-PCA ELISA (IgG) Cut-off: 20 U/ml U/ml |
|---|---|---|---|---|---|
| BS 2014-II-256 | 42 | M | 0.014 | 4835 | 12 |
| BS 2014-II-257 | 30 | F | 0.021 | 4098 | <2 |
| BS 2014-II-259 | 27 | F | 0.016 | 4306 | 8 |
| BS 2014-II-262 | 44 | M | 0.015 | 4165 | 2 |
| BS 2014-II-263 | 22 | M | 0.018 | 3922 | 6 |
| BS 2014-II-264 | 24 | M | 0.017 | 3305 | <2 |
| BS 2014-II-266 | 26 | M | 0.015 | 2285 | <2 |
| BS 2014-II-268 | 64 | M | 0.014 | 4419 | <2 |
| BS 2014-II-269 | 59 | M | 0.021 | 4057 | 6 |
| BS 2014-II-270 | 20 | F | 0.009 | 2941 | <2 |
| BS 2014-II-274 | 21 | M | 0.035 | 9391 | 2 |
| BS 2014-II-275 | 54 | M | 0.015 | 5130 | 2 |
| BS 2014-II-276 | 33 | F | 0.032 | 4446 | 4 |

TABLE 4

Results for the investigation of the sensitivity of the inventive assay by means of chemiluminescence (ChLIA)

| | Sample | RLU |
|---|---|---|
| AIG patients (n = 29) | 01122017-1 | 63 152 |
| | 01122017-2 | 21 014 |
| | 01122017-3 | 47 948 |
| | 01122017-4 | 64 709 |
| | 01122017-5 | 76 510 |
| | 01122017-6 | 57 101 |
| | 01122017-7 | 107 771 |
| | 01122017-8 | 96 252 |
| | 01122017-9 | 88 773 |
| | 01122017-10 | 101 609 |
| | 01122017-11 | 31 900 |
| | 01122017-12 | 53 679 |
| | 01122017-13 | 82 617 |
| | 01122017-14 | 136 471 |
| | 01122017-15 | 61 015 |
| | 01122017-16 | 50 633 |
| | 01122017-17 | 114 152 |
| | 01122017-18 | 143 291 |
| | 01122017-19 | 78 018 |
| | 01122017-20 | 56 620 |
| | 01122017-21 | 112 762 |
| | 01122017-22 | 56 937 |
| | 01122017-23 | 153 585 |
| | 01122017-24 | 87 705 |
| | 01122017-25 | 82 279 |
| | 01122017-26 | 89 876 |
| | 01122017-27 | 2712 |
| | 01122017-28 | 69 662 |
| | 01122017-29 | 84 330 |

The invention claimed is:

1. A method, comprising:

incubating a sample comprising antibodies from a patient having or suspected of having autoimmune gastritis with a carrier comprising a solid phase, the carrier having immobilized thereon an agent for specific capture of an autoantibody against a beta-subunit of gastric H+/K+-ATPase, wherein said agent is only provided from or is a mammalian cell and is one or more selected from the group consisting of:

an isolated or purified polypeptide comprising the beta-subunit of human gastric H+/K+-ATPase, or SEQ ID NO: 3 or SEQ ID NO: 5; and fixed cells comprising a polypeptide comprising the beta-subunit of human gastric H+/K+-ATPase, or SEQ ID NO: 3 or SEQ ID NO: 5; optionally wherein any of the polypeptides have a tag or detectable label, and detecting whether an autoantibody against the beta-subunit of gastric $H^+/K^+$-ATPase is present or not in the sample, wherein the beta-subunit of gastric H+/K+-ATPase is the sole biomarker tested for in the sample and the sole biomarker immobilized on the carrier.

2. The method according to claim 1, wherein the carrier is at least one selected from the group consisting of an immunofluorescence assay carrier comprising fixed cells, a lateral flow device, a cellulose-based polymer, a biochip, a microarray, and a chromatography column material.

3. The method according to claim 1, wherein the carrier is an ELISA microtiter plate.

4. The method according to claim 1, wherein the sample is at least one selected from the group consisting of serum, whole blood, plasma and cerebrospinal fluid.

5. The method according to claim 1, wherein the autoantibody is a class IgG antibody.

6. The method according to claim 2, wherein the carrier is the immunofluorescence assay carrier comprising fixed cells for a microscopic analysis.

7. A method, comprising:

incubating a sample comprising antibodies from a patient having or suspected of having autoimmune gastritis with a carrier comprising a solid phase, the carrier having immobilized thereon an agent for specific capture of an autoantibody against a beta-subunit of gastric H+/K+-ATPase, wherein the agent is selected from the group consisting of:

SEQ ID NO: 3 or SEQ ID NO: 5; and fixed cells comprising SEQ ID NO: 3 or SEQ ID NO: 5, and detecting whether an autoantibody against the beta-subunit of gastric $H^+/K^+$-ATPase is present or not in the sample, wherein the method does not comprise detecting whether an autoantibody against an alpha-subunit of gastric H+/K+-ATPase is present or not in the sample.

8. A method, comprising:

incubating a sample comprising antibodies from a patient having or suspected of having autoimmune gastritis with a carrier comprising a solid phase, the carrier having immobilized thereon an agent for specific capture of an autoantibody against a beta-subunit of gastric H+/K+-ATPase, wherein the agent is selected from the group consisting of:

SEQ ID NO: 3;

SEQ ID NO: 3 having a tag or detectable label; and fixed cells comprising SEQ ID NO: 3 or SEQ ID NO: 3 having a tag or detectable label, and detecting whether an autoantibody against the beta-subunit of gastric $H^+/K^+$-ATPase is present or not in the sample, wherein the method does not comprise detecting whether an autoantibody against an alpha-subunit of gastric $H^+/K^+$-ATPase is present or not in the sample.

9. A method, comprising:

incubating a sample comprising antibodies from a patient having or suspected of having autoimmune gastritis with a carrier comprising a solid phase, the carrier having immobilized thereon an agent for specific capture of an autoantibody against a beta-subunit of gastric H+/K+-ATPase, wherein the agent is selected from the group consisting of:

SEQ ID NO: 5;

SEQ ID NO: 5 having a tag or detectable label; and fixed cells comprising SEQ ID NO: 5 or SEQ ID NO: 5 having a tag or detectable label, and detecting whether an autoantibody against the beta-subunit of gastric $H^+/K^+$-ATPase is present or not in the sample, wherein the method does not comprise detecting whether an autoantibody against an alpha-subunit of gastric H+/K+-ATPase is present or not in the sample.

10. The method according to claim 1, wherein the carrier is a microtitre plate.

11. The method according to claim 1, wherein the carrier is a bead.

12. The method according to claim 1, wherein the carrier is a blot.

13. The method according to claim 1, wherein the carrier is at least one blot selected from the group consisting of western blot, line blot and dot blot.

14. The method according to claim 1, wherein said agent is one or more selected from the group consisting of:

an isolated or purified polypeptide comprising SEQ ID NO: 3 or SEQ ID NO: 5; and fixed cells comprising a polypeptide comprising SEQ ID NO: 3 or SEQ ID NO: 5;

optionally wherein any of the polypeptides have a tag or detectable label.

15. The method according to claim 1, wherein said agent is one or more selected from the group consisting of:

an isolated or purified polypeptide comprising SEQ ID NO: 3 or SEQ ID NO: 5; optionally wherein the polypeptide has a tag or detectable label.

16. The method according to claim 1, wherein said agent is one or more selected from the group consisting of:

an isolated or purified polypeptide comprising SEQ ID NO: 3 or SEQ ID NO: 5; and fixed cells comprising a polypeptide comprising the beta-subunit of human gastric H+/K+-ATPase, or SEQ ID NO: 3 or SEQ ID NO: 5;

optionally wherein any of the polypeptides have a tag or detectable label.

17. The method according to claim 1, wherein said agent is an isolated or purified polypeptide comprising the beta-subunit of human gastric H+/K+-ATPase.

18. The method according to claim 1, wherein said agent is fixed cells comprising a polypeptide comprising the beta-subunit of human gastric H+/K+-ATPase.

19. A method, comprising:

incubating a sample comprising antibodies from a patient having or suspected of having autoimmune gastritis with a carrier comprising a solid phase, the carrier having immobilized thereon an agent for specific capture of an autoantibody against a beta-subunit of gastric H+/K+-ATPase, wherein said agent is only provided from or is a mammalian cell and is one or more selected from the group consisting of:

an isolated or purified polypeptide comprising the beta-subunit of human gastric H+/K+-ATPase, or SEQ ID NO: 3 or SEQ ID NO: 5; and fixed cells comprising a polypeptide comprising the beta-subunit of human gastric H+/K+-ATPase, or SEQ ID NO: 3 or SEQ ID NO: 5; optionally wherein any of the polypeptides have a tag or detectable label, and detecting whether an autoantibody against the beta-subunit of gastric $H^+/K^+$-ATPase is present or not in the sample, wherein the autoantibody against the beta-subunit of gastric H+/K+-ATPase is the sole autoimmune biomarker derived from gastric H+/K+-ATPase tested for in the sample and the autoantibody against the beta-subunit of gastric H+/K+-ATPase is the sole autoimmune biomarker derived from gastric H+/K+-ATPase captured on the carrier.

* * * * *

SEQUENCE LISTING

```
<160> NUMBER OF SEQ ID NOS: 12

<210> SEQ ID NO 1
<211> LENGTH: 258
<212> TYPE: PRT
<213> ORGANISM: Artificial Sequence
<220> FEATURE:
<223> OTHER INFORMATION: spGh*-H6-ATP4B(ec)

<400> SEQUENCE: 1

Met Lys His Leu Trp Phe Phe Leu Leu Leu Val Ala Ala Pro Arg Trp
1               5                   10                  15

Val Leu Ser Gly Pro Met His His His His His His Met Ser Gln Thr
            20                  25                  30

Val Asp Pro Tyr Thr Pro Asp Tyr Gln Asp Gln Leu Arg Ser Pro Gly
        35                  40                  45

Val Thr Leu Arg Pro Asp Val Tyr Gly Glu Lys Gly Leu Glu Ile Val
    50                  55                  60

Tyr Asn Val Ser Asp Asn Arg Thr Trp Ala Asp Leu Thr Gln Thr Leu
65                  70                  75                  80

His Ala Phe Leu Ala Gly Tyr Ser Pro Ala Ala Gln Glu Asp Ser Ile
                85                  90                  95

Asn Cys Thr Ser Glu Gln Tyr Phe Phe Gln Glu Ser Phe Arg Ala Pro
            100                 105                 110

Asn His Thr Lys Phe Ser Cys Lys Phe Thr Ala Asp Met Leu Gln Asn
        115                 120                 125

Cys Ser Gly Leu Ala Asp Pro Asn Phe Gly Phe Glu Glu Gly Lys Pro
    130                 135                 140
```

-continued

```
Cys Phe Ile Ile Lys Met Asn Arg Ile Val Lys Phe Leu Pro Ser Asn
145                 150                 155                 160

Gly Ser Ala Pro Arg Val Asp Cys Ala Phe Leu Asp Gln Pro Arg Glu
                165                 170                 175

Leu Gly Gln Pro Leu Gln Val Lys Tyr Tyr Pro Pro Asn Gly Thr Phe
            180                 185                 190

Ser Leu His Tyr Phe Pro Tyr Tyr Gly Lys Lys Ala Gln Pro His Tyr
        195                 200                 205

Ser Asn Pro Leu Val Ala Ala Lys Leu Leu Asn Ile Pro Arg Asn Ala
    210                 215                 220

Glu Val Ala Ile Val Cys Lys Val Met Ala Glu His Val Thr Phe Asn
225                 230                 235                 240

Asn Pro His Asp Pro Tyr Glu Gly Lys Val Glu Phe Lys Leu Lys Ile
                245                 250                 255

Glu Lys


<210> SEQ ID NO 2
<211> LENGTH: 239
<212> TYPE: PRT
<213> ORGANISM: Artificial Sequence
<220> FEATURE:
<223> OTHER INFORMATION: H6-ATP4B(ec) extracellular domain, with
      N-terminal His tag

<400> SEQUENCE: 2

Gly Pro Met His His His His His His Met Ser Gln Thr Val Asp Pro
1               5                   10                  15

Tyr Thr Pro Asp Tyr Gln Asp Gln Leu Arg Ser Pro Gly Val Thr Leu
            20                  25                  30

Arg Pro Asp Val Tyr Gly Glu Lys Gly Leu Glu Ile Val Tyr Asn Val
        35                  40                  45

Ser Asp Asn Arg Thr Trp Ala Asp Leu Thr Gln Thr Leu His Ala Phe
    50                  55                  60

Leu Ala Gly Tyr Ser Pro Ala Ala Gln Glu Asp Ser Ile Asn Cys Thr
65                  70                  75                  80

Ser Glu Gln Tyr Phe Phe Gln Glu Ser Phe Arg Ala Pro Asn His Thr
                85                  90                  95

Lys Phe Ser Cys Lys Phe Thr Ala Asp Met Leu Gln Asn Cys Ser Gly
            100                 105                 110

Leu Ala Asp Pro Asn Phe Gly Phe Glu Glu Gly Lys Pro Cys Phe Ile
        115                 120                 125

Ile Lys Met Asn Arg Ile Val Lys Phe Leu Pro Ser Asn Gly Ser Ala
    130                 135                 140

Pro Arg Val Asp Cys Ala Phe Leu Asp Gln Pro Arg Glu Leu Gly Gln
145                 150                 155                 160

Pro Leu Gln Val Lys Tyr Tyr Pro Pro Asn Gly Thr Phe Ser Leu His
                165                 170                 175

Tyr Phe Pro Tyr Tyr Gly Lys Lys Ala Gln Pro His Tyr Ser Asn Pro
            180                 185                 190

Leu Val Ala Ala Lys Leu Leu Asn Ile Pro Arg Asn Ala Glu Val Ala
        195                 200                 205

Ile Val Cys Lys Val Met Ala Glu His Val Thr Phe Asn Asn Pro His
    210                 215                 220

Asp Pro Tyr Glu Gly Lys Val Glu Phe Lys Leu Lys Ile Glu Lys
225                 230                 235
```

<210> SEQ ID NO 3
<211> LENGTH: 228
<212> TYPE: PRT
<213> ORGANISM: Artificial Sequence
<220> FEATURE:
<223> OTHER INFORMATION: Extracellular domain of the ATP4B-subunit

<400> SEQUENCE: 3

```
Gln Thr Val Asp Pro Tyr Thr Pro Asp Tyr Gln Asp Gln Leu Arg Ser
1               5                   10                  15

Pro Gly Val Thr Leu Arg Pro Asp Val Tyr Gly Glu Lys Gly Leu Glu
            20                  25                  30

Ile Val Tyr Asn Val Ser Asp Asn Arg Thr Trp Ala Asp Leu Thr Gln
        35                  40                  45

Thr Leu His Ala Phe Leu Ala Gly Tyr Ser Pro Ala Ala Gln Glu Asp
    50                  55                  60

Ser Ile Asn Cys Thr Ser Glu Gln Tyr Phe Phe Gln Glu Ser Phe Arg
65                  70                  75                  80

Ala Pro Asn His Thr Lys Phe Ser Cys Lys Phe Thr Ala Asp Met Leu
                85                  90                  95

Gln Asn Cys Ser Gly Leu Ala Asp Pro Asn Phe Gly Phe Glu Glu Gly
            100                 105                 110

Lys Pro Cys Phe Ile Ile Lys Met Asn Arg Ile Val Lys Phe Leu Pro
        115                 120                 125

Ser Asn Gly Ser Ala Pro Arg Val Asp Cys Ala Phe Leu Asp Gln Pro
    130                 135                 140

Arg Glu Leu Gly Gln Pro Leu Gln Val Lys Tyr Tyr Pro Pro Asn Gly
145                 150                 155                 160

Thr Phe Ser Leu His Tyr Phe Pro Tyr Tyr Gly Lys Lys Ala Gln Pro
                165                 170                 175

His Tyr Ser Asn Pro Leu Val Ala Ala Lys Leu Leu Asn Ile Pro Arg
            180                 185                 190

Asn Ala Glu Val Ala Ile Val Cys Lys Val Met Ala Glu His Val Thr
        195                 200                 205

Phe Asn Asn Pro His Asp Pro Tyr Glu Gly Lys Val Glu Phe Lys Leu
    210                 215                 220

Lys Ile Glu Lys
225
```

<210> SEQ ID NO 4
<211> LENGTH: 23
<212> TYPE: PRT
<213> ORGANISM: Artificial Sequence
<220> FEATURE:
<223> OTHER INFORMATION: Transmembrane domain of the ATP4B-subunit

<400> SEQUENCE: 4

```
Ser Leu Tyr Tyr Val Ala Phe Tyr Val Val Met Thr Gly Leu Phe Ala
1               5                   10                  15

Leu Cys Leu Tyr Val Leu Met
            20
```

<210> SEQ ID NO 5
<211> LENGTH: 25
<212> TYPE: PRT
<213> ORGANISM: Artificial Sequence
<220> FEATURE:
<223> OTHER INFORMATION: Immunodominant epitope of the human ATP4B-
      subunit -continued

<400> SEQUENCE: 5

```
Leu Leu Asn Ile Pro Arg Asn Ala Glu Val Ala Ile Val Cys Lys Val
1               5                   10                  15

Met Ala Glu His Val Thr Phe Asn Asn
            20                  25
```

<210> SEQ ID NO 6
<211> LENGTH: 25
<212> TYPE: PRT
<213> ORGANISM: Artificial Sequence
<220> FEATURE:
<223> OTHER INFORMATION: Immunodominant epitope of the murine ATP4B-subunit

<400> SEQUENCE: 6

```
Leu Leu Asn Val Pro Lys Asn Met Gln Val Ser Ile Val Cys Lys Ile
1               5                   10                  15

Leu Ala Asp His Val Thr Phe Asn Asn
            20                  25
```

<210> SEQ ID NO 7
<211> LENGTH: 291
<212> TYPE: PRT
<213> ORGANISM: Artificial Sequence
<220> FEATURE:
<223> OTHER INFORMATION: The ATP4B-subunit amino acid sequence represented in P51164

<400> SEQUENCE: 7

```
Met Ala Ala Leu Gln Glu Lys Lys Thr Cys Gly Gln Arg Met Glu Glu
1               5                   10                  15

Phe Gln Arg Tyr Cys Trp Asn Pro Asp Thr Gly Gln Met Leu Gly Arg
            20                  25                  30

Thr Leu Ser Arg Trp Val Trp Ile Ser Leu Tyr Tyr Val Ala Phe Tyr
        35                  40                  45

Val Val Met Thr Gly Leu Phe Ala Leu Cys Leu Tyr Val Leu Met Gln
    50                  55                  60

Thr Val Asp Pro Tyr Thr Pro Asp Tyr Gln Asp Gln Leu Arg Ser Pro
65                  70                  75                  80

Gly Val Thr Leu Arg Pro Asp Val Tyr Gly Glu Lys Gly Leu Glu Ile
                85                  90                  95

Val Tyr Asn Val Ser Asp Asn Arg Thr Trp Ala Asp Leu Thr Gln Thr
            100                 105                 110

Leu His Ala Phe Leu Ala Gly Tyr Ser Pro Ala Ala Gln Glu Asp Ser
        115                 120                 125

Ile Asn Cys Thr Ser Glu Gln Tyr Phe Phe Gln Glu Ser Phe Arg Ala
    130                 135                 140

Pro Asn His Thr Lys Phe Ser Cys Lys Phe Thr Ala Asp Met Leu Gln
145                 150                 155                 160

Asn Cys Ser Gly Leu Ala Asp Pro Asn Phe Gly Phe Glu Glu Gly Lys
                165                 170                 175

Pro Cys Phe Ile Ile Lys Met Asn Arg Ile Val Lys Phe Leu Pro Ser
            180                 185                 190

Asn Gly Ser Ala Pro Arg Val Asp Cys Ala Phe Leu Asp Gln Pro Arg
        195                 200                 205

Glu Leu Gly Gln Pro Leu Gln Val Lys Tyr Tyr Pro Pro Asn Gly Thr
    210                 215                 220
```

-continued

```
Phe Ser Leu His Tyr Phe Pro Tyr Tyr Gly Lys Lys Ala Gln Pro His
225                 230                 235                 240

Tyr Ser Asn Pro Leu Val Ala Ala Lys Leu Leu Asn Ile Pro Arg Asn
                245                 250                 255

Ala Glu Val Ala Ile Val Cys Lys Val Met Ala Glu His Val Thr Phe
            260                 265                 270

Asn Asn Pro His Asp Pro Tyr Glu Gly Lys Val Glu Phe Lys Leu Lys
        275                 280                 285

Ile Glu Lys
    290


<210> SEQ ID NO 8
<211> LENGTH: 19
<212> TYPE: PRT
<213> ORGANISM: Artificial Sequence
<220> FEATURE:
<223> OTHER INFORMATION: Immunodominant epitope of the murine ATP4A-
      subunit

<400> SEQUENCE: 8

Pro Leu Leu Cys Val Gly Leu Arg Ala Gln Trp Glu Asp His His Leu
1               5                   10                  15

Gln Asp Leu


<210> SEQ ID NO 9
<211> LENGTH: 1035
<212> TYPE: PRT
<213> ORGANISM: Artificial Sequence
<220> FEATURE:
<223> OTHER INFORMATION: Alpha-subunit of the gastric H+/K+-ATPase
      (P20648)

<400> SEQUENCE: 9

Met Gly Lys Ala Glu Asn Tyr Glu Leu Tyr Ser Val Glu Leu Gly Pro
1               5                   10                  15

Gly Pro Gly Gly Asp Met Ala Ala Lys Met Ser Lys Lys Lys Lys Ala
            20                  25                  30

Gly Gly Gly Gly Gly Lys Arg Lys Glu Lys Leu Glu Asn Met Lys Lys
        35                  40                  45

Glu Met Glu Ile Asn Asp His Gln Leu Ser Val Ala Glu Leu Glu Gln
    50                  55                  60

Lys Tyr Gln Thr Ser Ala Thr Lys Gly Leu Ser Ala Ser Leu Ala Ala
65                  70                  75                  80

Glu Leu Leu Leu Arg Asp Gly Pro Asn Ala Leu Arg Pro Pro Arg Gly
                85                  90                  95

Thr Pro Glu Tyr Val Lys Phe Ala Arg Gln Leu Ala Gly Gly Leu Gln
            100                 105                 110

Cys Leu Met Trp Val Ala Ala Ala Ile Cys Leu Ile Ala Phe Ala Ile
        115                 120                 125

Gln Ala Ser Glu Gly Asp Leu Thr Thr Asp Asp Asn Leu Tyr Leu Ala
    130                 135                 140

Ile Ala Leu Ile Ala Val Val Val Val Thr Gly Cys Phe Gly Tyr Tyr
145                 150                 155                 160

Gln Glu Phe Lys Ser Thr Asn Ile Ile Ala Ser Phe Lys Asn Leu Val
                165                 170                 175

Pro Gln Gln Ala Thr Val Ile Arg Asp Gly Asp Lys Phe Gln Ile Asn
            180                 185                 190
```

-continued

```
Ala Asp Gln Leu Val Val Gly Asp Leu Val Glu Met Lys Gly Gly Asp
        195                 200                 205

Arg Val Pro Ala Asp Ile Arg Ile Leu Ala Ala Gln Gly Cys Lys Val
    210                 215                 220

Asp Asn Ser Ser Leu Thr Gly Glu Ser Glu Pro Gln Thr Arg Ser Pro
225                 230                 235                 240

Glu Cys Thr His Glu Ser Pro Leu Glu Thr Arg Asn Ile Ala Phe Phe
                245                 250                 255

Ser Thr Met Cys Leu Glu Gly Thr Val Gln Gly Leu Val Val Asn Thr
            260                 265                 270

Gly Asp Arg Thr Ile Ile Gly Arg Ile Ala Ser Leu Ala Ser Gly Val
        275                 280                 285

Glu Asn Glu Lys Thr Pro Ile Ala Ile Glu Ile Glu His Phe Val Asp
    290                 295                 300

Ile Ile Ala Gly Leu Ala Ile Leu Phe Gly Ala Thr Phe Phe Ile Val
305                 310                 315                 320

Ala Met Cys Ile Gly Tyr Thr Phe Leu Arg Ala Met Val Phe Phe Met
                325                 330                 335

Ala Ile Val Val Ala Tyr Val Pro Glu Gly Leu Leu Ala Thr Val Thr
            340                 345                 350

Val Cys Leu Ser Leu Thr Ala Lys Arg Leu Ala Ser Lys Asn Cys Val
        355                 360                 365

Val Lys Asn Leu Glu Ala Val Glu Thr Leu Gly Ser Thr Ser Val Ile
    370                 375                 380

Cys Ser Asp Lys Thr Gly Thr Leu Thr Gln Asn Arg Met Thr Val Ser
385                 390                 395                 400

His Leu Trp Phe Asp Asn His Ile His Thr Ala Asp Thr Thr Glu Asp
                405                 410                 415

Gln Ser Gly Gln Thr Phe Asp Gln Ser Ser Glu Thr Trp Arg Ala Leu
            420                 425                 430

Cys Arg Val Leu Thr Leu Cys Asn Arg Ala Ala Phe Lys Ser Gly Gln
        435                 440                 445

Asp Ala Val Pro Val Pro Lys Arg Ile Val Ile Gly Asp Ala Ser Glu
    450                 455                 460

Thr Ala Leu Leu Lys Phe Ser Glu Leu Thr Leu Gly Asn Ala Met Gly
465                 470                 475                 480

Tyr Arg Asp Arg Phe Pro Lys Val Cys Glu Ile Pro Phe Asn Ser Thr
                485                 490                 495

Asn Lys Phe Gln Leu Ser Ile His Thr Leu Glu Asp Pro Arg Asp Pro
            500                 505                 510

Arg His Leu Leu Val Met Lys Gly Ala Pro Glu Arg Val Leu Glu Arg
        515                 520                 525

Cys Ser Ser Ile Leu Ile Lys Gly Gln Glu Leu Pro Leu Asp Glu Gln
    530                 535                 540

Trp Arg Glu Ala Phe Gln Thr Ala Tyr Leu Ser Leu Gly Gly Leu Gly
545                 550                 555                 560

Glu Arg Val Leu Gly Phe Cys Gln Leu Tyr Leu Asn Glu Lys Asp Tyr
                565                 570                 575

Pro Pro Gly Tyr Ala Phe Asp Val Glu Ala Met Asn Phe Pro Ser Ser
            580                 585                 590

Gly Leu Cys Phe Ala Gly Leu Val Ser Met Ile Asp Pro Pro Arg Ala
        595                 600                 605
```

-continued

```
Thr Val Pro Asp Ala Val Leu Lys Cys Arg Thr Ala Gly Ile Arg Val
    610                 615                 620

Ile Met Val Thr Gly Asp His Pro Ile Thr Ala Lys Ala Ile Ala Ala
625                 630                 635                 640

Ser Val Gly Ile Ile Ser Glu Gly Ser Glu Thr Val Glu Asp Ile Ala
                645                 650                 655

Ala Arg Leu Arg Val Pro Val Asp Gln Val Asn Arg Lys Asp Ala Arg
            660                 665                 670

Ala Cys Val Ile Asn Gly Met Gln Leu Lys Asp Met Asp Pro Ser Glu
        675                 680                 685

Leu Val Glu Ala Leu Arg Thr His Pro Glu Met Val Phe Ala Arg Thr
    690                 695                 700

Ser Pro Gln Gln Lys Leu Val Ile Val Glu Ser Cys Gln Arg Leu Gly
705                 710                 715                 720

Ala Ile Val Ala Val Thr Gly Asp Gly Val Asn Asp Ser Pro Ala Leu
                725                 730                 735

Lys Lys Ala Asp Ile Gly Val Ala Met Gly Ile Ala Gly Ser Asp Ala
            740                 745                 750

Ala Lys Asn Ala Ala Asp Met Ile Leu Leu Asp Asp Asn Phe Ala Ser
        755                 760                 765

Ile Val Thr Gly Val Glu Gln Gly Arg Leu Ile Phe Asp Asn Leu Lys
    770                 775                 780

Lys Ser Ile Ala Tyr Thr Leu Thr Lys Asn Ile Pro Glu Leu Thr Pro
785                 790                 795                 800

Tyr Leu Ile Tyr Ile Thr Val Ser Val Pro Leu Pro Leu Gly Cys Ile
                805                 810                 815

Thr Ile Leu Phe Ile Glu Leu Cys Thr Asp Ile Phe Pro Ser Val Ser
            820                 825                 830

Leu Ala Tyr Glu Lys Ala Glu Ser Asp Ile Met His Leu Arg Pro Arg
        835                 840                 845

Asn Pro Lys Arg Asp Arg Leu Val Asn Glu Pro Leu Ala Ala Tyr Ser
    850                 855                 860

Tyr Phe Gln Ile Gly Ala Ile Gln Ser Phe Ala Gly Phe Thr Asp Tyr
865                 870                 875                 880

Phe Thr Ala Met Ala Gln Glu Gly Trp Phe Pro Leu Leu Cys Val Gly
                885                 890                 895

Leu Arg Ala Gln Trp Glu Asp His His Leu Gln Asp Leu Gln Asp Ser
            900                 905                 910

Tyr Gly Gln Glu Trp Thr Phe Gly Gln Arg Leu Tyr Gln Gln Tyr Thr
        915                 920                 925

Cys Tyr Thr Val Phe Phe Ile Ser Ile Glu Val Cys Gln Ile Ala Asp
    930                 935                 940

Val Leu Ile Arg Lys Thr Arg Arg Leu Ser Ala Phe Gln Gln Gly Phe
945                 950                 955                 960

Phe Arg Asn Lys Ile Leu Val Ile Ala Ile Val Phe Gln Val Cys Ile
                965                 970                 975

Gly Cys Phe Leu Cys Tyr Cys Pro Gly Met Pro Asn Ile Phe Asn Phe
            980                 985                 990

Met Pro Ile Arg Phe Gln Trp Trp  Leu Val Pro Leu Pro  Tyr Gly Ile
        995                 1000                1005

Leu Ile  Phe Val Tyr Asp Glu  Ile Arg Lys Leu Gly  Val Arg Cys
    1010                1015                1020
```

```
Cys Pro  Gly Ser Trp Trp Asp  Gln Glu Leu Tyr Tyr
    1025                 1030                1035


<210> SEQ ID NO 10
<211> LENGTH: 417
<212> TYPE: PRT
<213> ORGANISM: Artificial Sequence
<220> FEATURE:
<223> OTHER INFORMATION: Intrinsic factor (NP_005133.2)

<400> SEQUENCE: 10

Met Ala Trp Phe Ala Leu Tyr Leu Leu Ser Leu Leu Trp Ala Thr Ala
1               5                   10                  15

Gly Thr Ser Thr Gln Thr Gln Ser Ser Cys Ser Val Pro Ser Ala Gln
            20                  25                  30

Glu Pro Leu Val Asn Gly Ile Gln Val Leu Met Glu Asn Ser Val Thr
        35                  40                  45

Ser Ser Ala Tyr Pro Asn Pro Ser Ile Leu Ile Ala Met Asn Leu Ala
    50                  55                  60

Gly Ala Tyr Asn Leu Lys Ala Gln Lys Leu Leu Thr Tyr Gln Leu Met
65                  70                  75                  80

Ser Ser Asp Asn Asn Asp Leu Thr Ile Gly Gln Leu Gly Leu Thr Ile
                85                  90                  95

Met Ala Leu Thr Ser Ser Cys Arg Asp Pro Gly Asp Lys Val Ser Ile
            100                 105                 110

Leu Gln Arg Gln Met Glu Asn Trp Ala Pro Ser Ser Pro Asn Ala Glu
        115                 120                 125

Ala Ser Ala Phe Tyr Gly Pro Ser Leu Ala Ile Leu Ala Leu Cys Gln
    130                 135                 140

Lys Asn Ser Glu Ala Thr Leu Pro Ile Ala Val Arg Phe Ala Lys Thr
145                 150                 155                 160

Leu Leu Ala Asn Ser Ser Pro Phe Asn Val Asp Thr Gly Ala Met Ala
                165                 170                 175

Thr Leu Ala Leu Thr Cys Met Tyr Asn Lys Ile Pro Val Gly Ser Glu
            180                 185                 190

Glu Gly Tyr Arg Ser Leu Phe Gly Gln Val Leu Lys Asp Ile Val Glu
        195                 200                 205

Lys Ile Ser Met Lys Ile Lys Asp Asn Gly Ile Ile Gly Asp Ile Tyr
    210                 215                 220

Ser Thr Gly Leu Ala Met Gln Ala Leu Ser Val Thr Pro Glu Pro Ser
225                 230                 235                 240

Lys Lys Glu Trp Asn Cys Lys Lys Thr Thr Asp Met Ile Leu Asn Glu
                245                 250                 255

Ile Lys Gln Gly Lys Phe His Asn Pro Met Ser Ala Ile Gln Ile Leu
            260                 265                 270

Pro Ser Leu Lys Gly Lys Thr Tyr Leu Asp Val Pro Gln Val Thr Cys
        275                 280                 285

Ser Pro Asp His Glu Val Gln Pro Thr Leu Pro Ser Asn Pro Gly Pro
    290                 295                 300

Gly Pro Thr Ser Ala Ser Asn Ile Thr Val Ile Tyr Thr Ile Asn Asn
305                 310                 315                 320

Gln Leu Arg Gly Val Glu Leu Leu Phe Asn Glu Thr Ile Asn Val Ser
                325                 330                 335

Val Lys Ser Gly Ser Val Leu Leu Val Val Leu Glu Glu Ala Gln Arg
            340                 345                 350
```

-continued

```
Lys Asn Pro Met Phe Lys Phe Glu Thr Thr Met Thr Ser Trp Gly Leu
        355                 360                 365

Val Val Ser Ser Ile Asn Asn Ile Ala Glu Asn Val Asn His Lys Thr
    370                 375                 380

Tyr Trp Gln Phe Leu Ser Gly Val Thr Pro Leu Asn Glu Gly Val Ala
385                 390                 395                 400

Asp Tyr Ile Pro Phe Asn His Glu His Ile Thr Ala Asn Phe Thr Gln
                405                 410                 415

Tyr


<210> SEQ ID NO 11
<211> LENGTH: 8752
<212> TYPE: DNA
<213> ORGANISM: Artificial Sequence
<220> FEATURE:
<223> OTHER INFORMATION: cDNA encoding the ATP4A-subunit ligated into
      the vector pTriEx

<400> SEQUENCE: 11

ggggaattgt gagcggataa caattccccg gagttaatcc gggaccttta attcaaccca     60

acacaatata ttatagttaa ataagaatta ttatcaaatc atttgtatat taattaaaat    120

actatactgt aaattacatt ttatttacaa tcaaaggaga tataggccgt caaggcccac    180

catggggaag gccgagaact atgagctcta ctcggtggag ctgggtcctg gccctggcgg    240

ggacatggct gccaagatga gcaagaagaa gaaggcgggt ggcgggggtg gcaagaggaa    300

ggagaagctg gagaacatga agaaggagat ggagattaac gaccaccagc tgtcagtggc    360

ggagctggaa cagaaatacc agaccagtgc caccaagggc ctctctgcga gcctggctgc    420

tgagctgctg ctgcgggatg ggcccaacgc actgcggcca ccacggggca ccccagagta    480

cgtcaagttc gcgaggcagc tggccggggg cctgcagtgc ctcatgtggg ttgccgccgc    540

catctgcctc atcgcctttg ccatccaggc tagtgagggg gacctcacca ccgacgacaa    600

tctgtacctg gcaatcgctc tcattgctgt ggttgtcgtc accggctgct ttggctacta    660

ccaggaattc aagagcacca acatcatcgc cagctttaag aaccttgtgc cacagcaagc    720

cactgtcatc cgcgatggag acaaattcca gatcaacgct gaccaactgg tggtgggcga    780

cctggtggag atgaaaggtg ggacagagt gcccgccgac atccgcatcc tggcggccca    840

gggctgcaag gtggacaact cctcgctgac aggggagtct gagccacaga cccgctcacc    900

cgagtgcacg cacgagagcc ctctggagac ccgcaacatc gccttcttct ccaccatgtg    960

ccttgagggc accgtgcagg gcctggtggt gaacacgggc gaccgcacca tcattgggcg   1020

catcgcatcg ctggcgtcgg gggtggaaaa cgagaagaca cccatcgcta tcgagatcga   1080

gcattttgtg gacatcatcg cgggcctggc cattctcttc ggtgccacat tttttattgt   1140

ggccatgtgc attggctaca ccttcctgcg ggccatggtc ttcttcatgg ccatcgtggt   1200

ggcctatgtg cctgaggggc tgctggccac tgtcacagtc tgcctgtccc tgacagccaa   1260

gcgcctggcc agtaagaact gcgtggtcaa gaacctggag gcggtggaga cattgggctc   1320

cacttcggtg atctgctcgg acaagacagg gactctcact cagaaccgca tgactgtgtc   1380

ccatctgtgg tttgacaacc acatccacac agctgacacc acggaagacc agtcagggca   1440

gacgtttgac cagtcctcgg agacgtggcg ggcgctgtgc cgggtgctca ccctgtgcaa   1500

ccgcgccgcc ttcaagtccg gccaggatgc agtgcctgtg cccaagcgca tcgtgattgg   1560

agacgcatcg gagacggcgc tgctcaagtt ctcggagctg acgctgggca acgccatggg   1620
```

-continued

```
ctaccgggac cgcttcccaa aagtctgcga gatacccttc aactccacca acaagttcca   1680
gctgtccatc catacgctgg aggacccgcg ggacccgcga cacttgctgg tgatgaaggg   1740
cgcccccgag cgcgtgctgg agcgctgcag ctccatcctt atcaagggcc aggagctgcc   1800
gctggacgag cagtggcgcg aggccttcca gaccgcctac ctcagcctgg gaggcctggg   1860
cgaacgcgtg ctcggcttct gccagctcta cctgaatgag aaggactacc cgcctggcta   1920
tgccttcgac gtagaggcca tgaactttcc atctagcggc ctctgctttg cgggacttgt   1980
atccatgatt gacccacccc gggccaccgt ccctgatgct gtgctcaagt gtcgcaccgc   2040
aggcatccgg gtgatcatgg taacgggtga ccaccccatc accgccaagg ccattgcagc   2100
cagtgtgggc atcatctcgg aaggcagcga gacagtggag gacatcgctg cccgcctccg   2160
tgtgcccgta gaccaggtta atcgcaagga tgcccgtgcc tgtgtgatca atggcatgca   2220
gctgaaggac atggacccat cggaactggt cgaggccctg cgcacccacc ccgagatggt   2280
gtttgcgcgc accagccccc agcagaagct ggtgatcgtg gagagctgcc agcggctggg   2340
tgcgattgtg gccgtcacgg gggatggtgt gaatgactcc ccagctctga agaaggcaga   2400
catcggagta gccatgggca tcgctggctc agatgctgcc aaaaatgcag ctgacatgat   2460
cctgctggat gacaactttg cctccattgt gacaggcgtg gagcagggtc gactgatctt   2520
cgacaacctg aagaagtcta ttgcctacac attgaccaag aacatcccag agctgacacc   2580
ctacctcatc tacatcaccg tcagcgtgcc cctgcccctc gggtgcatca ccatcctctt   2640
catcgaactc tgcactgaca ttttcccatc tgtgtccctg gcatatgaaa aggccgagag   2700
tgacatcatg cacctgcgtc cacgcaaccc aaagcgtgac agattggtca acgagcccct   2760
ggctgcctac tcctacttcc agattggtgc cattcagtcc tttgctggct tcactgacta   2820
cttcacggca atggcccagg agggctggtt cccactgctg tgcgtggggc tgcgggcgca   2880
gtgggaggac caccacctac aagatctgca ggacagctac ggccaggagt ggacattcgg   2940
gcagcgcctg taccagcagt acacctgcta caccgtgttc ttcatcagca ttgaggtgtg   3000
ccagatcgcc gatgtcctca tccgcaagac gcgccgtctc tctgccttcc agcaaggctt   3060
cttcaggaat aagatcctgg tgatcgccat cgtgttccag gtctgcatcg gctgcttcct   3120
gtgctactgc cccggcatgc ccaacatctt caacttcatg cccattcggt tccagtggtg   3180
gctggtcccc ctgccctacg gcatcctcat cttcgtctat gatgagatcc ggaagcttgg   3240
agttcgctgt tgcccaggga gctggtggga ccaggaactc tactattagg gcctcatggg   3300
ccggcgcgcc caccaccacc accaccactg acactaagtg attaacctca ggtgcaggct   3360
gcctatcaga aggtggtggc tggtgtggcc aatgccctgg ctcacaaata ccactgagat   3420
cgatcttttt ccctctgcca aaaattatgg ggacatcatg aagccccttg agcatctgac   3480
ttctggctaa taaaggaaat ttattttcat tgcaatagtg tgttggaatt ttttgtgtct   3540
ctcactcgga aggacatatg ggagggcaaa tcatttaaaa catcagaatg agtatttggt   3600
ttagagtttg gcaacatatg cccatatgta actagcataa ccccttgggg cctctaaacg   3660
ggtcttgagg ggtttttgc tgaaagcatg cggaggaaat tctccttgaa gtttccctgg   3720
tgttcaaagt aaaggagttt gcaccagacg cacctctgtt cactggtccg gcgtattaaa   3780
acacgataca ttgttattag tacatttatt aagcgctaga ttctgtgcgt tgttgattta   3840
cagacaattg ttgtacgtat tttaataatt cattaaattt ataatcttta gggtggtatg   3900
ttagagcgaa aatcaaatga ttttcagcgt ctttatatct gaatttaaat attaaatcct   3960
```

-continued

```
caatagattt gtaaaatagg tttcgattag tttcaaacaa gggttgtttt tccgaaccga   4020
tggctggact atctaatgga ttttcgctca acgccacaaa acttgccaaa tcttgtagca   4080
gcaatctagc tttgtcgata ttcgtttgtg ttttgttttg taataaaggt tcgacgtcgt   4140
tcaaaatatt atgcgctttt gtatttcttt catcactgtc gttagtgtac aattgactcg   4200
acgtaaacac gttaaataga gcttggacat atttaacatc gggcgtgtta gctttattag   4260
gccgattatc gtcgtcgtcc caaccctcgt cgttagaagt tgcttccgaa gacgattttg   4320
ccatagccac acgacgccta ttaattgtgt cggctaacac gtccgcgatc aaatttgtag   4380
ttgagctttt tggaattatt tctgattgcg ggcgtttttg ggcgggtttc aatctaactg   4440
tgcccgattt taattcagac aacacgttag aaagcgatgg tgcaggcggt ggtaacattt   4500
cagacggcaa atctactaat ggcggcggtg gtggagctga tgataaatct accatcggtg   4560
gaggcgcagg cggggctggc ggcggaggcg gaggcggagg tggtggcggt gatgcagacg   4620
gcggtttagg ctcaaatgtc tctttaggca acacagtcgg cacctcaact attgtactgg   4680
tttcgggcgc cgtttttggt ttgaccggtc tgagacgagt gcgatttttt tcgtttctaa   4740
tagcttccaa caattgttgt ctgtcgtcta aaggtgcagc gggttgaggt tccgtcggca   4800
ttggtggagc gggcggcaat tcagacatcg atggtggtgg tggtggtgga ggcgctggaa   4860
tgttaggcac gggagaaggt ggtggcggcg gtgccgccgg tataatttgt tctggtttag   4920
tttgttcgcg cacgattgtg ggcaccggcg caggcgccgc tggctgcaca acggaaggtc   4980
gtctgcttcg aggcagcgct tggggtggtg gcaattcaat attataattg gaatacaaat   5040
cgtaaaaatc tgctataagc attgtaattt cgctatcgtt taccgtgccg atatttaaca   5100
accgctcaat gtaagcaatt gtattgtaaa gagattgtct caagctcgga acgctgcgct   5160
cggtcgttcg gctgcggcga gcggtatcag ctcactcaaa ggcggtaata cggttatcca   5220
cagaatcagg ggataacgca ggaaagaaca tgtgagcaaa aggccagcaa aaggccagga   5280
accgtaaaaa ggccgcgttg ctggcgtttt tccataggct ccgcccccct gacgagcatc   5340
acaaaaatcg acgctcaagt cagaggtggc gaaacccgac aggactataa agataccagg   5400
cgtttccccc tggaagctcc ctcgtgcgct ctcctgttcc gaccctgccg cttaccggat   5460
acctgtccgc ctttctccct tcgggaagcg tggcgctttc tcaatgctca cgctgtaggt   5520
atctcagttc ggtgtaggtc gttcgctcca agctgggctg tgtgcacgaa ccccccgttc   5580
agcccgaccg ctgcgcctta tccggtaact atcgtcttga gtccaacccg gtaagacacg   5640
acttatcgcc actggcagca gccactggta acaggattag cagagcgagg tatgtaggcg   5700
gtgctacaga gttcttgaag tggtggccta actacggcta cactagaagg acagtatttg   5760
gtatctgcgc tctgctgaag ccagttacct tcggaaaaag agttggtagc tcttgatccg   5820
gcaaacaaac caccgctggt agcggtggtt tttttgtttg caagcagcag attacgcgca   5880
gaaaaaaagg atctcaagaa gatcctttgt taccaatgct taatcagtga ggcacctatc   5940
tcagcgatct gtctatttcg ttcatccata gttgcctgac tccccgtcgt gtagataact   6000
acgatacggg agggcttacc atctggcccc agtgctgcaa tgataccgcg agacccacgc   6060
tcaccggctc cagatttatc agcaataaac cagccagccg gaagggccga gcgcagaagt   6120
ggtcctgcaa ctttatccgc ctccatccag tctattaatt gttgccggga agctagagta   6180
agtagttcgc cagttaatag tttgcgcaac gttgttgcca ttgctacagg catcgtggtg   6240
tcacgctcgt cgtttggtat ggcttcattc agctccggtt cccaacgatc aaggcgagtt   6300
acatgatccc ccatgttgtg caaaaaagcg gttagctcct tcggtcctcc gatcgttgtc   6360
```

-continued

```
agaagtaagt tggccgcagt gttatcactc atggttatgg cagcactgca taattctctt   6420
actgtcatgc catccgtaag atgcttttct gtgactggtg agtactcaac caagtcattc   6480
tgagaatagt gtatgcggcg accgagttgc tcttgcccgg cgtcaatacg ggataatacc   6540
gcgccacata gcagaacttt aaaagtgctc atcattggaa aacgttcttc ggggcgaaaa   6600
ctctcaagga tcttaccgct gttgagatcc agttcgatgt aacccactcg tgcacccaac   6660
tgatcttcag catcttttac tttcaccagc gtttctgggt gagcaaaaac aggaaggcaa   6720
aatgccgcaa aaaagggaat aagggcgaca cggaaatgtt gaatactcat actcttcctt   6780
tttcaatatt attgaagcat ttatcagggt tattgtctca tgtccgcgcg tttcctgcat   6840
cttttaatca aatcccaaga tgtgtataaa ccaccaaact gccaaaaaat gaaaactgtc   6900
gacaagctct gtccgtttgc tggcaactgc aagggtctca atcctatttg taattattga   6960
ataataaaac aattataaat gtcaaatttg tttttttatta acgatacaaa ccaaacgcaa   7020
caagaacatt tgtagtatta tctataattg aaaacgcgta gttataatcg ctgaggtaat   7080
atttaaaatc attttcaaat gattcacagt taatttgcga caatataatt ttattttcac   7140
ataaactaga cgccttgtcg tcttcttctt cgtattcctt ctctttttca tttttctctt   7200
cataaaaatt aacatagtta ttatcgtatc catatatgta tctatcgtat agagtaaatt   7260
ttttgttgtc ataaatatat atgtcttttt taatggggtg tatagtaccg ctgcgcatag   7320
tttttctgta atttacaaca gtgctatttt ctggtagttc ttcggagtgt gttgctttaa   7380
ttattaaatt tatataatca atgaatttgg gatcgtcggt tttgtacaat atgttgccgg   7440
catagtacgc agcttcttct agttcaatta caccattttt tagcagcacc ggattaacat   7500
aactttccaa aatgttgtac gaaccgttaa acaaaaacag ttcacctccc ttttctatac   7560
tattgtctgc gagcagttgt ttgttgttaa aaataacagc cattgtaatg agacgcacaa   7620
actaatatca caaactggaa atgtctatca atatatagtt gctctagtta ttaatagtaa   7680
tcaattacgg ggtcattagt tcatagccca tatatggagt tccgcgttac ataacttacg   7740
gtaaatggcc cgcctggctg accgcccaac gacccccgcc cattgacgtc aataatgacg   7800
tatgttccca tagtaacgcc aatagggact ttccattgac gtcaatgggt ggactattta   7860
cggtaaactg cccacttggc agtacatcaa gtgtatcata tgccaagtac gccccctatt   7920
gacgtcaatg acggtaaatg gcccgcctgg cattatgccc agtacatgac cttatgggac   7980
tttcctactt ggcagtacat ctacgtatta gtcatcgcta ttaccatgca tggtcgaggt   8040
gagccccacg ttctgcttca ctctccccat ctcccccccc tccccacccc caattttgta   8100
tttatttatt ttttaattat tttgtgcagc gatgggggcg gggggggggg gggggcgcgc   8160
gccaggcggg gcggggcggg gcgaggggcg gggcggggcg aggcggagag gtgcggcggc   8220
agccaatcag agcggcgcgc tccgaaagtt tccttttatg gcgaggcggc ggcggcggcg   8280
gccctataaa aagcgaagcg cgcggcgggc gggagtcgct gcgacgctgc cttcgccccg   8340
tgccccgctc cgccgccgcc tcgcgccgcc cgcccggct ctgactgacc gcgttactcc   8400
cacaggtgag cgggcgggac ggcccttctc cttcgggctg taattagcgc ttggtttaat   8460
gacggcttgt ttcttttctg tggctgcgtg aaagccttga ggggctccgg gagggccctt   8520
tgtgcggggg gagcggctcg ggctgtccg cggggggacg gctgccttcg gggggacgg   8580
```

```
ggcagggcgg ggttcggctt ctggcgtgtg accggcggct ctagagcctc tgctaaccat   8640

gttcatgcct tcttcttttt cctacagctc ctgggcaacg tgctggttat tgtgctgtct   8700

catcattttg gcaaagaatt ggatcggacc gaaattaata cgactcacta ta           8752
```

```
<210> SEQ ID NO 12
<211> LENGTH: 6490
<212> TYPE: DNA
<213> ORGANISM: Artificial Sequence
<220> FEATURE:
<223> OTHER INFORMATION: cDNA encoding the ATP4B-subunit ligated into
      the vector pTriEx

<400> SEQUENCE: 12
```

```
ggggaattgt gagcggataa caattccccg gagttaatcc gggaccttta attcaaccca     60

acacaatata ttatagttaa ataagaatta ttatcaaatc atttgtatat taattaaaat    120

actatactgt aaattacatt ttatttacaa tcaaaggaga tataccatgg cggctctgca    180

ggagaagaag acgtgtggcc agcgcatgga ggagttccag cgttactgct ggaacccgga    240

cacggggcag atgctgggcc gcaccctgtc ccggtgggtg tggatcagcc tgtactacgt    300

ggccttctac gtggtgatga ctgggctctt cgccctgtgc ctctatgtgc tgatgcagac    360

agtggacccg tacacaccgg actaccaaga ccagctacgg tcaccagggg taaccttaag    420

gccggatgtt tacggggaga aaggcctgga aattgtctac aacgtctctg ataacagaac    480

ctgggcagac ctcacacaga ctctccacgc cttcctagca ggctactctc cagcagccca    540

ggaggacagc atcaactgca cctccgagca gtacttcttc caggagagtt tccgcgctcc    600

caaccacacc aagttctcct gcaagttcac ggcagatatg ctgcagaact gctcaggcct    660

ggcggatccc aacttcggct ttgaagaagg aaagccatgt tttattatta aaatgaacag    720

gatcgtcaag ttcctcccca gcaacggctc ggcccccaga gtggactgcg ccttcctgga    780

ccagccccgc gagctcggcc agccgctgca ggtcaagtac taccctccca acggcacctt    840

cagtctgcac tacttccctt attacgggaa gaaagcccag ccccactaca gcaacccccct   900

ggtggcagcg aagctcctca acatccccag gaacgctgag gtcgccatcg tgtgcaaggt    960

catggcagag cacgtgacct tcaacaatcc ccacgacccg tatgaaggga aagtggagtt   1020

caaactcaag attgagaagt gactcgagca ccaccatcac catcaccatc actaagtgat   1080

taacctcagg tgcaggctgc ctatcagaag gtggtggctg gtgtggccaa tgccctggct   1140

cacaaatacc actgagatcg atctttttcc ctctgccaaa aattatgggg acatcatgaa   1200

gccccttgag catctgactt ctggctaata aaggaaattt attttcattg caatagtgtg   1260

ttggaatttt ttgtgtctct cactcggaag gacatatggg agggcaaatc atttaaaaca   1320

tcagaatgag tatttggttt agagtttggc aacatatgcc catatgtaac tagcataacc   1380

ccttggggcc tctaaacggg tcttgagggg ttttttgctg aaagcatgcg gaggaaattc   1440

tccttgaagt ttccctggtg ttcaaagtaa aggagtttgc accagacgca cctctgttca   1500

ctggtccggc gtattaaaac acgatacatt gttattagta catttattaa gcgctagatt   1560

ctgtgcgttg ttgatttaca gacaattgtt gtacgtattt taataattca ttaaatttat   1620

aatctttagg gtggtatgtt agagcgaaaa tcaaatgatt ttcagcgtct ttatatctga   1680

atttaaatat taaatcctca atagatttgt aaaataggtt tcgattagtt tcaaacaagg   1740

gttgtttttc cgaaccgatg gctggactat ctaatggatt ttcgctcaac gccacaaaac   1800

ttgccaaatc ttgtagcagc aatctagctt tgtcgatatt cgtttgtgtt ttgttttgta   1860
```

-continued

```
ataaaggttc gacgtcgttc aaaatattat gcgcttttgt atttctttca tcactgtcgt   1920
tagtgtacaa ttgactcgac gtaaacacgt taaatagagc ttggacatat ttaacatcgg   1980
gcgtgttagc tttattaggc cgattatcgt cgtcgtccca accctcgtcg ttagaagttg   2040
cttccgaaga cgattttgcc atagccacac gacgcctatt aattgtgtcg gctaacacgt   2100
ccgcgatcaa atttgtagtt gagctttttg gaattatttc tgattgcggg cgtttttggg   2160
cgggtttcaa tctaactgtg cccgatttta attcagacaa cacgttagaa agcgatggtg   2220
caggcggtgg taacatttca gacggcaaat ctactaatgg cggcggtggt ggagctgatg   2280
ataaatctac catcggtgga ggcgcaggcg gggctggcgg cggaggcgga ggcggaggtg   2340
gtggcggtga tgcagacggc ggtttaggct caaatgtctc tttaggcaac acagtcggca   2400
cctcaactat tgtactggtt tcgggcgccg tttttggttt gaccggtctg agacgagtgc   2460
gatttttttc gtttctaata gcttccaaca attgttgtct gtcgtctaaa ggtgcagcgg   2520
gttgaggttc cgtcggcatt ggtggagcgg gcggcaattc agacatcgat ggtggtggtg   2580
gtggtggagg cgctggaatg ttaggcacgg gagaaggtgg tggcggcggt gccgccggta   2640
taatttgttc tggtttagtt tgttcgcgca cgattgtggg caccggcgca ggcgccgctg   2700
gctgcacaac ggaaggtcgt ctgcttcgag gcagcgcttg ggtggtggc aattcaatat   2760
tataattgga atacaaatcg taaaaatctg ctataagcat tgtaatttcg ctatcgttta   2820
ccgtgccgat atttaacaac cgctcaatgt aagcaattgt attgtaaaga gattgtctca   2880
agctcggaac gctgcgctcg gtcgttcggc tgcggcgagc ggtatcagct cactcaaagg   2940
cggtaatacg gttatccaca gaatcagggg ataacgcagg aaagaacatg tgagcaaaag   3000
gccagcaaaa ggccaggaac cgtaaaaagg ccgcgttgct ggcgtttttc cataggctcc   3060
gcccccctga cgagcatcac aaaaatcgac gctcaagtca gaggtggcga aacccgacag   3120
gactataaag ataccaggcg tttccccctg gaagctccct cgtgcgctct cctgttccga   3180
ccctgccgct taccggatac ctgtccgcct ttctcccttc gggaagcgtg gcgctttctc   3240
aatgctcacg ctgtaggtat ctcagttcgg tgtaggtcgt tcgctccaag ctgggctgtg   3300
tgcacgaacc ccccgttcag cccgaccgct gcgccttatc cggtaactat cgtcttgagt   3360
ccaacccggt aagacacgac ttatcgccac tggcagcagc cactggtaac aggattagca   3420
gagcgaggta tgtaggcggt gctacagagt tcttgaagtg gtggcctaac tacggctaca   3480
ctagaaggac agtatttggt atctgcgctc tgctgaagcc agttaccttc ggaaaaagag   3540
ttggtagctc ttgatccggc aaacaaacca ccgctggtag cggtggtttt tttgtttgca   3600
agcagcagat tacgcgcaga aaaaaaggat ctcaagaaga tcctttgtta ccaatgctta   3660
atcagtgagg cacctatctc agcgatctgt ctatttcgtt catccatagt tgcctgactc   3720
cccgtcgtgt agataactac gatacgggag ggcttaccat ctggccccag tgctgcaatg   3780
ataccgcgag acccacgctc accggctcca gatttatcag caataaacca gccagccgga   3840
agggccgagc gcagaagtgg tcctgcaact ttatccgcct ccatccagtc tattaattgt   3900
tgccgggaag ctagagtaag tagttcgcca gttaatagtt tgcgcaacgt tgttgccatt   3960
gctacaggca tcgtggtgtc acgctcgtcg tttggtatgg cttcattcag ctccggttcc   4020
caacgatcaa ggcgagttac atgatccccc atgttgtgca aaaaagcggt tagctccttc   4080
ggtcctccga tcgttgtcag aagtaagttg gccgcagtgt tatcactcat ggttatggca   4140
gcactgcata attctcttac tgtcatgcca tccgtaagat gcttttctgt gactggtgag   4200
```

-continued

```
tactcaacca agtcattctg agaatagtgt atgcggcgac cgagttgctc ttgcccggcg   4260
tcaatacggg ataataccgc gccacatagc agaactttaa aagtgctcat cattggaaaa   4320
cgttcttcgg ggcgaaaact ctcaaggatc ttaccgctgt tgagatccag ttcgatgtaa   4380
cccactcgtg cacccaactg atcttcagca tcttttactt tcaccagcgt ttctgggtga   4440
gcaaaaacag gaaggcaaaa tgccgcaaaa aagggaataa gggcgacacg gaaatgttga   4500
atactcatac tcttcctttt tcaatattat tgaagcattt atcagggtta ttgtctcatg   4560
tccgcgcgtt tcctgcatct tttaatcaaa tcccaagatg tgtataaacc accaaactgc   4620
caaaaaatga aaactgtcga caagctctgt ccgtttgctg gcaactgcaa gggtctcaat   4680
cctatttgta attattgaat aataaaacaa ttataaatgt caaatttgtt ttttattaac   4740
gatacaaacc aaacgcaaca agaacatttg tagtattatc tataattgaa aacgcgtagt   4800
tataatcgct gaggtaatat ttaaaatcat tttcaaatga ttcacagtta atttgcgaca   4860
atataatttt attttcacat aaactagacg ccttgtcgtc ttcttcttcg tattccttct   4920
ctttttcatt tttctcttca taaaaattaa catagttatt atcgtatcca tatatgtatc   4980
tatcgtatag agtaaatttt ttgttgtcat aaatatatat gtctttttta atggggtgta   5040
tagtaccgct gcgcatagtt tttctgtaat ttacaacagt gctattttct ggtagttctt   5100
cggagtgtgt tgctttaatt attaaattta tataatcaat gaatttggga tcgtcggttt   5160
tgtacaatat gttgccggca tagtacgcag cttcttctag ttcaattaca ccattttttta   5220
gcagcaccgg attaacataa ctttccaaaa tgttgtacga accgttaaac aaaaacagtt   5280
cacctccctt ttctatacta ttgtctgcga gcagttgttt gttgttaaaa ataacagcca   5340
ttgtaatgag acgcacaaac taatatcaca aactggaaat gtctatcaat atatagttgc   5400
tctagttatt aatagtaatc aattacgggg tcattagttc atagcccata tatggagttc   5460
cgcgttacat aacttacggt aaatggcccg cctggctgac cgcccaacga cccccgccca   5520
ttgacgtcaa taatgacgta tgttcccata gtaacgccaa tagggacttt ccattgacgt   5580
caatgggtgg actatttacg gtaaactgcc cacttggcag tacatcaagt gtatcatatg   5640
ccaagtacgc cccctattga cgtcaatgac ggtaaatggc ccgcctggca ttatgcccag   5700
tacatgacct tatgggactt tcctacttgg cagtacatct acgtattagt catcgctatt   5760
accatgcatg gtcgaggtga gccccacgtt ctgcttcact ctccccatct cccccccctc   5820
cccaccccca attttgtatt tatttatttt ttaattattt tgtgcagcga tgggggcggg   5880
gggggggggg gggcgcgcgc caggcggggc ggggcggggc gaggggcggg gcggggcgag   5940
gcggagaggt gcggcggcag ccaatcagag cggcgcgctc cgaaagtttc cttttatggc   6000
gaggcggcgg cggcggcggc cctataaaaa gcgaagcgcg cggcgggcgg gagtcgctgc   6060
gacgctgcct tcgccccgtg ccccgctccg ccgccgcctc gcgccgcccg ccccggctct   6120
gactgaccgc gttactccca caggtgagcg ggcgggacgg cccttctcct tcgggctgta   6180
attagcgctt ggtttaatga cggcttgttt cttttctgtg gctgcgtgaa agccttgagg   6240
ggctccggga gggccctttg tgcgggggga gcggctcggg gctgtccgcg gggggacggc   6300
tgccttcggg ggggacgggg cagggcgggg ttcggcttct ggcgtgtgac cggcggctct   6360
agagcctctg ctaaccatgt tcatgccttc ttcttttttcc tacagctcct gggcaacgtg   6420
ctggttattg tgctgtctca tcattttggc aaagaattgg atcggaccga aattaatacg   6480
actcactata                                                          6490
```